(12) United States Patent
Strong et al.

(10) Patent No.: US 9,226,917 B2
(45) Date of Patent: Jan. 5, 2016

(54) PHOTODYNAMIC THERAPY FOR CONDITIONS OF THE EYE

(75) Inventors: H. Andrew Strong, North Vancouver (CA); Yong Hao, Vancouver (CA)

(73) Assignee: Valeant Pharmaceuticals International, Inc. (CA)

( * ) Notice: Subject to any disclaimer, the term of this patent is extended or adjusted under 35 U.S.C. 154(b) by 923 days.

(21) Appl. No.: 13/140,411

(22) PCT Filed: Dec. 16, 2009

(86) PCT No.: PCT/CA2009/001857
§ 371 (c)(1),
(2), (4) Date: Nov. 7, 2011

(87) PCT Pub. No.: WO2010/069073
PCT Pub. Date: Jun. 24, 2010

(65) Prior Publication Data
US 2012/0041356 A1    Feb. 16, 2012

Related U.S. Application Data

(60) Provisional application No. 61/138,059, filed on Dec. 16, 2008, provisional application No. 61/182,943, filed on Jun. 1, 2009.

(51) Int. Cl.
| | |
|---|---|
| *A61K 31/409* | (2006.01) |
| *A61K 31/555* | (2006.01) |
| *A61K 31/573* | (2006.01) |
| *A61K 39/395* | (2006.01) |
| *C07K 16/22* | (2006.01) |
| *A61K 41/00* | (2006.01) |
| *A61K 39/00* | (2006.01) |

(52) U.S. Cl.
CPC ............. *A61K 31/409* (2013.01); *A61K 31/573* (2013.01); *A61K 39/395* (2013.01); *A61K 41/0071* (2013.01); *C07K 16/22* (2013.01); *A61K 2039/505* (2013.01); *C07K 2317/24* (2013.01)

(58) Field of Classification Search
CPC ............................ A61K 31/409; A61K 31/573
USPC ..................................... 514/185, 410
See application file for complete search history.

(56) References Cited

U.S. PATENT DOCUMENTS

| | | | |
|---|---|---|---|
| 2003/0083649 A1 | 5/2003 | Margaron et al. | |
| 2007/0072933 A1 | 3/2007 | Peyman | |
| 2012/0244147 A1* | 9/2012 | Theuer et al. ............... | 424/133.1 |

FOREIGN PATENT DOCUMENTS

| | | |
|---|---|---|
| CA | 2 437 557 A1 | 8/2002 |
| CA | 2 437 561 A1 | 8/2002 |
| WO | WO 02/062385 A2 | 8/2002 |
| WO | WO 03/039404 A2 | 5/2003 |
| WO | WO 2004/080284 A2 | 9/2004 |
| WO | WO 2007/038453 A2 | 4/2007 |
| WO | WO 2010/069073 A1 | 6/2010 |

OTHER PUBLICATIONS

Ahmadieh, H., et al., "Single-session photodynamic therapy combined with intravitreal bevacizumab and triamcinolone for neovascular age-related macular degeneration," *BMC Ophthalmology* 7(10): 6 pages, BioMed Central Ltd., England (Jun. 2007).

Augustin, A.J., et al., "Verteporfin Therapy Combined with Intravitreal Triamcinolone in All Types of Choroidal Neovascularization due to Age-Related Macular Degeneration," *Ophthalmology* 113(1):14-22. The American Academy of Ophthalmology, Elsevier Inc., United States (2006).

Augustin, A.J., and Offermann, I., "Combination Therapy for Choroidal Neovascularisation," *Drugs Aging* 24(12):979-990, Adis Data Information BV, New Zealand (Dec. 2007).

Augustin, A.J., et al., "Triple Therapy for Choroidal Neovascularization Due to Age-Related Macular Degeneration," *Retina, The Journal of Retinal Vitreous Diseases* 27(2):133-140, Ophthalmic Communications Society, Inc., The Netherlands (Feb. 2007).

Bradley, J., et al., "Combination therapy for the treatment of ocular neovascularization," *Angiogenesis* 10:141-148, Springer Science+Business Media B.V., United States (Jun. 2007).

Heier, J.S., et al., "Ranibizumab Combined With Verteporfin Photodynamic Therapy in Neovascular Age-Reglated Macular Degeneration," *Arch Ophthalmol* 124:1532-1543, American Medical Association, United States (2006).

Husain, D., et al., "Safety and Efficacy of Intravitreal Injection of Ranibizumab in Combination With Verteporfin PDT on Experimental Choroidal Neovascularization in the Monkey," *Arch Ophthalmol* 123:509-516, American Medical Association, United States (2005).

Kabeel, M.M., et al., "Combined intravitreal bevacizumab and photodynamic therapy with vertiporfin for management of choroidal neovascularization secondary to age-related macular degeneration," *Clinical Ophthalmology* 2(1):159-166, Dove Medical Press, New Zealand (Mar. 2008).

Spitzer, M.S., et al., "Treatment of age-related macular degeneration: focus on ranibizumab," *Clinical Ophthalmology* 2(1):1-14, Dove Medical Press, United States (Mar. 2008).

Zuluaga, M-F., et al., "Synergies of VEGF Inhibition and Photodynamic Therapy in the Treatment of Age-Related Macular Degeneration," *IOVS* 48(4):1767-1772, Association for Research in Vision and Ophthalmology, United States (Apr. 2007).

(Continued)

*Primary Examiner* — Zohreh Fay
(74) *Attorney, Agent, or Firm* — John E. Thomas; Harter Secrest & Emery LLP

(57) ABSTRACT

The use of a combination of photodynamic therapy and an anti-VEGF agent in the treatment of conditions characterized by unwanted choroidal neovasculature is described. These conditions include wet age-related macular degeneration Preferred anti-VEGF agents are antibodies such as bevacizumab or ranibizumab Photosensitizers may be selected from green porphyrins such as BPD-MA (verteporfin) and the photodynamic activation of the photo sensitizer may be accomplished using a reduced fluence rate. The use may further comprises an anti-inflammatory agent such as dexamethasone.

21 Claims, 25 Drawing Sheets

(56) References Cited

OTHER PUBLICATIONS

*Visual Acuity Measurement Standard—ICO 1984*, Unanimously approved by the Visual Functions Committee, St. Margherita Ligure Italy May 25, 1984, Presented to the Consilium Opthalmologicum Universale and approved for distribution Oct. 5, 1984, Published in the Italian Journal of Ophthalmology 1988, 18 pages.

"QLT Announces Positive Results From the Evaluation of Visudyne® Combination Therapy," QLT Inc., Jun. 2, 2009, accessed at http://www.qltinc.com/newsCenter/2009/090602.htm, 3 pages, Canada.

"QLT Completes Enrollment in the Radical Study," QLT, Inc., May 5, 2008 accessed at http://www.qltinc.com/newsCenter/2008/080505.htm, 2 pages, Canada.

"Positive results from Visudyne® combination therapy study reported at Annual Macula Society Conference," QLT Inc. via PR Newswire, Mar. 28, 2008 accessed at http://www.qltinc.com/newsCenter/2008/080328.htm, 2 pages, Canada.

United States Clinical Trial, NCT00492284 "A multicenter, randomized, single-masked study comprising reduced-fluence Visudyne®-Lucentis® combination therapies and Lucentis® Monotherapy in subjects with CNV secondary to AMD," May 30, 2008, accessed at clinicaltrials.gov/ct2/show/NC00492287?term=nct00492284, 3 pages, United States.

United States Clinical Trial, NCT00359164 "A Randomized, Controlled, Double-Masked, Phase II Pilot Study of Visudyne® Photodynamic Therapy (PDT) (Low and Very Low Fluence) Combined with Bevacizumab (Avastin), in Patients With Subfoveal Choroidal Neovascularization (CNV) Secondary to Age Related Macular Degeneration (AMD)," Aug. 12, 2008, accessed at clinicaltrials.gov/ct2/show/NC00359164?term=nct00359164, 3 pages, United States.

"QLT Announces 12-Month Results From Novartis Sponsored Mont Blanc Study Evaluating Standard-Fluence Visudyne® Combination Therapy," QLT Inc., Jun. 15, 2009 accessed at accessed at http://www.qltinc.com/newscenter/2009/090615.htm, 3 pages, Canada.

International Search Report for International Application No. PCT/CA2009/001857, Canadian Intellectual Property Office, Canada, mailed on Apr. 8, 2010.

European Search Report for EP Application No. 09 832 787, Munich, Germany, mailed on May 10, 2012.

* cited by examiner

Figure 1
Inclusion Criteria

- 50 years of age or older
- Treatment naïve (except for laser treatment outside the subfoveal area) for choroidal neovascularization (CNV) due to AMD in the study eye
- Subfoveal CNV due to AMD
- CNV must be ≥50% of the entire lesion
- All lesion composition types with a lesion greatest linear dimension (GLD) ≤5400 microns (approx ≤9 disc areas [DA])
- Best-corrected Early Treatment Diabetic Retinopathy Study (ETDRS) VA score of 25 - 73 letters (approximate Snellen equivalent of 20/40 - 20/320)

Figure 2
Exclusion Criteria

- Subfoveal geographic atrophy or subfoveal fibrosis in the study eye
- Intraocular surgery within 3 months of enrollment
- Uncontrolled glaucoma (i.e., subject is on >1 glaucoma medication or has glaucoma that could lead to progressive visual field deterioration
- Recent (<1 year) history of stroke
- Inability to attend the protocol-required visits
- Known allergies or hypersensitivity to any of the study treatments

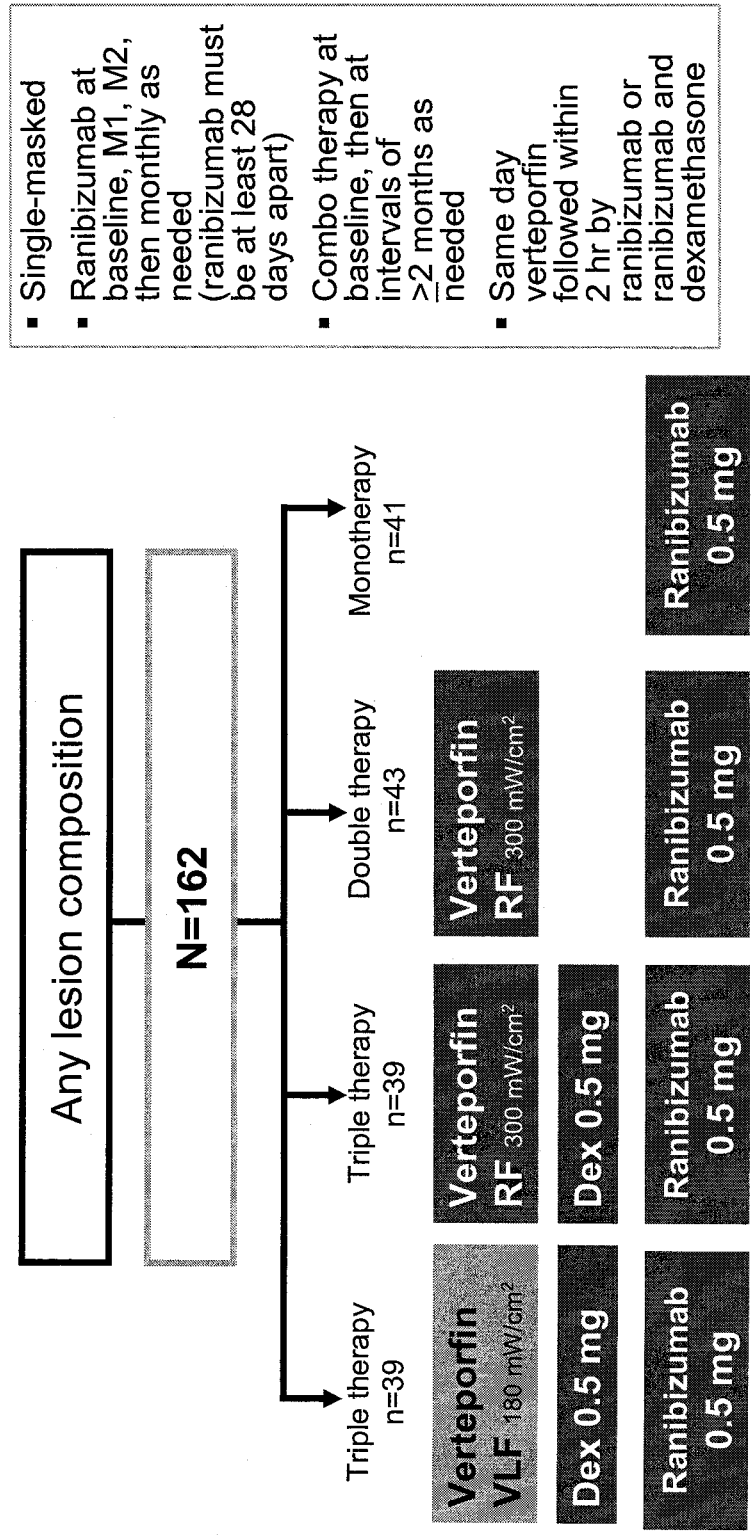

Treatment Schedule

Retreatment Criteria

Figure 6
Patient Baseline Characteristics

| Characteristic | VRD VLF N=39 | VRD RF N=39 | VR Double N=43 | Ranibizumab N=41 |
|---|---|---|---|---|
| Visual Acuity, letters | | | | |
| Mean | 58.1 | 55.6 | 53.3 | 56.0 |
| Median | 61.0 | 58.0 | 56.0 | 60.0 |
| Central retinal thickness (μm), mean | 318.3 | 337.3 | 337.3 | 311.9 |
| GLD (μm), mean | 2778.8 | 2740.1 | 2796.1 | 3118.4 |

VA Change From Baseline:
% Subjects Who Gained ≥0 letters VA

Cumulative Number of Retreatments Based on Either OCT or FA

Cumulative Number of Retreatments Based on Meeting FA Criteria

Cumulative Number of Retreatments
Based on Meeting OCT vs FA Criteria

Figure 16
Summary of Adverse Events (AEs)

|  | VRD VLF (N=39) | VRD RF (N=39) | Double (N=43) | Ranibizumab (N=41) |
|---|---|---|---|---|
| All AEs | 28 (71.8%) | 35 (89.7%) | 33 (76.7%) | 34 (82.9%) |
| All Associated AEs | 13 (33.3%) | 14 (35.9%) | 17 (39.5%) | 9 (22.0%) |
| All Study Eye Ocular AE | 18 (46.2%) | 19 (48.7%) | 22 (51.2%) | 20 (48.8%) |
| All Associated Ocular AEs | 11 (28.2%) | 11 (28.2%) | 11 (25.6%) | 9 (22.0%) |
| All SAEs | 4 (10.3%) | 10 (25.6%) | 8 (18.6%) | 8 (19.5%) |
| All Associated SAEs | 1 (2.6%) | 2 (5.1%) | 0 | 0 |
| All Associated Ocular SAEs | 1 (2.6%) | 2 (5.1%) | 0 | 0 |

Figure 17
Ocular AEs Related to Treatment

|  | VRD VLF (N=39) | VRD RF (N=39) | Double (N=43) | Ranibizumab (N=41) |
|---|---|---|---|---|
| All Associated Ocular AEs | 11 (28.2%) | 11 (28.2%) | 11 (25.6%) | 9 (22.0%) |
| Cataract | 0 | 1 (2.6%) | 3 (7.0%) | 0 |
| Choroidal hypoperfusion | 0 | 0 | 2 (4.7%) | 0 |
| Glaucoma | 0 | 0 | 1 (2.3%) | 0 |
| Increased IOP | 1 (2.6%) | 5 (12.8%) | 3 (7.0%) | 5 (12.2%) |
| Retinal disorder | 3 (7.7%) | 2 (5.2%) | 0 | 0 |
| Vision abnormal | 4 (10.3%) | 1 (2.6%) | 6 (14.0%) | 3 (7.3%) |
| Vision decreased | 4 (10.3%) | 3 (7.7%) | 5 (11.6%) | 0 |
| Visual field defect | 3 (7.7%) | 1 (2.6%) | 2 (4.7%) | 1 (2.4%) |

Figure 18
BSL Lesion Composition

| Lesion Composition | VLD VLF (N=39) | VLD HF (N=39) | Double (N=43) | Lucentis (N=41) |
|---|---|---|---|---|
| Minimally classic | 6 (15%) | 4 (10%) | 9 (21%) | 8 (20%) |
| Occult | 10 (26%) | 16 (41%) | 20 (47%) | 18 (44%) |
| Predominantly classic | 23 (59%) | 19 (49%) | 14 (33%) | 15 (37%) |

Figure 20
VA Change From Baseline: Subjects
Who Lost <15 Letters

| | ¼ Fluence Triple | | ½ Fluence Triple | | Double | | Lucentis | |
|---|---|---|---|---|---|---|---|---|
| | n | % | n | % | n | % | n | % |
| Month 3 | 38 | 92% | 37 | 97% | 40 | 100% | 38 | 97% |
| Month 6 | 36 | 92% | 34 | 100% | 37 | 97% | 37 | 89% |
| Month 9 | 36 | 83% | 32 | 91% | 36 | 92% | 32 | 88% |
| Month 12 | 37 | 86% | 34 | 91% | 33 | 91% | 32 | 91% |

Figure 21
VA Change From Baseline: Subjects Who Gained ≥15 Letters

| | ¼ Fluence Triple | | ½ Fluence Triple | | Double | | Lucentis | |
|---|---|---|---|---|---|---|---|---|
| | n | % | n | % | n | % | n | % |
| Month 3 | 38 | 11% | 37 | 19% | 40 | 18% | 38 | 21% |
| Month 6 | 36 | 22% | 34 | 24% | 37 | 16% | 37 | 19% |
| Month 9 | 36 | 19% | 32 | 28% | 36 | 19% | 32 | 31% |
| Month 12 | 37 | 27% | 34 | 35% | 33 | 24% | 32 | 22% |

Figure 22
Central Retinal Thickness (µm)
Mean Change from Baseline

| | ¼ Fluence Triple | | | ½ Fluence Triple | | | Double | | | Lucentis | | |
|---|---|---|---|---|---|---|---|---|---|---|---|---|
| | N | mean | diff | N | mean | diff | N | mean | diff | N | mean | diff |
| Day 0 | 38 | 314.6 | | 39 | 337.3 | | 42 | 341.3 | | 40 | 313.2 | |
| Month 3 | 38 | 216.8 | -98 | 37 | 209.7 | -125 | 40 | 207.0 | -138 | 38 | 210.9 | -104 |
| Month 6 | 36 | 210.9 | -108 | 34 | 205.9 | -130 | 37 | 223.5 | -123 | 37 | 220.9 | -94 |
| Month 9 | 36 | 198.0 | -110 | 32 | 206.8 | -116 | 36 | 199.1 | -144 | 33 | 208.5 | -97 |
| Month 12 | 37 | 200.6 | -112 | 34 | 199.8 | -133 | 33 | 201.2 | -123 | 32 | 207.5 | -109 |

Figure 24
Summary of AEs at 12 months (Subjects Level)

| | ¼ Fluence Triple (N=39) | ½ Fluence Triple (N=39) | Double (N=43) | Lucentis (N=41) |
|---|---|---|---|---|
| All AEs | 35 (89.7%) | 35 (89.7%) | 35 (81.4%) | 37 (90.2%) |
| All Associated AEs | 17 (43.6%) | 16 (41.0%) | 21 (48.8%) | 11 (26.8%) |
| All Study Eye Ocular AEs | 21 (53.8%) | 23 (59.0%) | 25 (58.1%) | 23 (56.1%) |
| All Associated Ocular AEs | 13 (33.3%) | 13 (33.3%) | 14 (32.6%) | 11 (26.8%) |
| All SAEs | 7 (17.9%) | 11 (28.2%) | 13 (30.2%) | 14 (34.1%) |
| All Associated SAEs | 2 (5.1%) | 2 (5.1%) | 1 (2.3%) | 0 |
| All Associated Ocular SAEs | 2 (5.1%) | 2 (5.1%) | 1 (2.3%) | 0 |

Figure 25
Associated Treatment Site Ocular AEs by Subject and Event at 12 months

| | ¼ Fluence Triple | | ½ Fluence Triple | | Double | | Lucentis | |
|---|---|---|---|---|---|---|---|---|
| | Sub. | Event | Sub. | Event | Sub. | Event | Sub. | Event |
| Vision abnormal | 4 (10.3%) | 5 | 2 (5.1%) | 2 | 2 (4.7%) | 3 | 0 | 0 |
| Vision decrease | 3 (7.7%) | 3 | 3 (7.7%) | 3 | 2 (4.7%) | 2 | 0 | 0 |
| Visual field defect | 4 (10.3%) | 4 | 0 | 0 | 2 (4.7%) | 2 | 2 (4.9%) | 2 |
| Retinal detachment | 0 | 0 | 0 | 0 | 1 (2.3%) | 1 | 0 | 0 |
| Retinal disorder | 0 | 0 | 0 | 0 | 1 (2.3%) | 1 | 0 | 0 |
| Retinal tear | 1 (2.6%) | 1 | 0 | 0 | 0 | 0 | 0 | 0 |
| Increased IOP | 0 | 0 | 4 (10.3%) | 8 | 3 (7.0%) | 3 | 0 | 0 |

PHOTODYNAMIC THERAPY FOR CONDITIONS OF THE EYE

CROSS-REFERENCE TO RELATED APPLICATIONS

This application is the national phase of PCT application PCT/CA2009/001857 having an international filing date of 16 Dec. 2009, which claims priority of U.S. provisional application Ser. Nos. 61/138,059 filed 16 Dec. 2008, and 61/182,943 filed 1 Jun. 2009. The contents of these documents are incorporated herein by reference in their entirety.

FIELD OF THE INVENTION

This invention generally relates to methods of photodynamic therapy and compositions for treating ocular conditions. More particularly, this invention relates to the use of photodynamic therapy used in conjunction with one or more additional therapies, more particularly anti-VEGF agents and anti-inflammatory agents, in the treatment of conditions characterized by unwanted or undesired neovasculature in the eye.

BACKGROUND

Neovascularization occurs when either there is proliferation of blood vessels in tissues that would otherwise not contain or there is a growth of a different kind of blood vessel in a tissue. Unwanted neovascularization is associated with a number of disease conditions, such as that seen to occur with tumor growth or vision loss. One example of undesirable neovascularization in the eye is choroidal neovasculature (CNV) like that found in the "wet" form of age-related macular degeneration (AMD).

AMD causes severe, irreversible vision loss and is the leading cause of blindness in individuals older than 50 years in the Western World. Most patients have the non-neovascular ("dry") form, characterized by drusen and abnormalities of the retinal pigment epithelium (RPE). Eighty to ninety percent of the severe vision loss due to AMD, however, is attributable to the form characterized by CNV, also called "wet" AMD. In the United States, between 70,000 to 200,000 individuals over the age of 65 develop the neovascular form of AMD every year (Bressler, N. "Submacular surgery: Are randomized trials necessary?" Arch Ophthalmol. 1995; 113; 1557-1560; Klein, R. et al. "The five-year incidence and progression of age-related maculopathy: the Beaver Dam Eye Study." Ophthalmol. 1997; 104(1):7-21).

In CNV, the newly formed vessels have a tendency to leak blood and fluid, causing symptoms of scotoma and metamorphopsia (Macular Photocoagulation Study Group. "Argon laser photocoagulation for neovascular maculopathy. Three-year results from randomized clinical trials." Arch Ophthalmol. 1986; 104:694-701). The new vessels are accompanied by proliferation of fibrous tissue (Macular Photocoagulation Study Group. "Laser photocoagulation of subfoveal neovascular lesions of age-related macular degeneration. Updated findings from two clinical trials." Arch Ophthalmol. 1993; 111:1200-1209). This complex of new vessels and fibrous tissue can destroy photoreceptors within 3 to 24 months. At the same time that existing CNV is destroying retinal tissue where it has formed, the lesion can continue to grow throughout the macula, resulting in progressive, severe and irreversible vision loss. Without treatment, most affected eyes will have poor central vision (<20/200) within 2 years (Macular Photocoagulation Study Group. "Recurrent choroidal neovascularization after argon laser photocoagulation for neovascular maculopathy." Arch Ophthalmol. 1986; 104:503-512). In addition, when one eye of an individual develops CNV, the fellow eye has about a 50% chance of developing a similar CNV lesion within 5 years (Treatment of Age-related Macular Degeneration With Photodynamic Therapy (TAP) Study Group. "Photodynamic therapy of subfoveal choroidal neovascularization in age-related macular degeneration with VISUDYNE: One-year results of 2 randomized clinical trials—TAP report 1." Arch Ophthalmol. 1999; 117:1329-1345).

Photodynamic therapy (PDT) offers an approach to selectively destroy CNV without significant destruction of overlying retina tissue, possibly by occluding the new vessels within the CNV lesion. Photodynamic therapy is a two-step process consisting of an intravenous injection of a photosensitizer (light-activated drug) followed by light application (Marcus, S. "Photodynamic therapy of human cancer: clinical status, potential and needs." In: Gomer C, ed. Future Directions and Application In Photodynamic Therapy. Berlingham: SPIE Press. 1990; IS6:5-56; Manyak, M. J. et al. "Photodynamic therapy." J Clin Oncol. 1988; 6:380-391; Roberts, W. G. et al. "Role of neovasculature and vascular permeability on the tumor retention of photodynamic agents." Cancer Res. 1992; 52(4):924-930). The light sources most commonly used are non-thermal lasers or light emitting diodes (LEDs). Photosensitizers may preferentially accumulate in neovascular tissues, including the endothelial cells of choroidal neovascularization. In combination with localized light administration, this allows for selective treatment of the pathologic tissue (Kreimer-Birmbaum, M. "Modified porphyrins, chlorins, phthalocyanines, and purpurins: second generation photosensitizers for photodynamic therapy." Semin Hematol. 1989; 26:157-173; Moan, J. et al. "Photosensitizing efficiencies, tumor and cellular uptake of different Photosensitizing drugs relevant for photodynamic therapy of cancer." Photochem Photobiol. 1987; 46:713-721). After exposure to light at a wavelength of 689 nm, an energy transfer cascade is initiated, culminating in the formation of singlet oxygen which generates intracellular free radicals (Kreimer-Birmbaum, M., supra; Roberts, W. G. et al. "In vitro photosensitization I. Cellular uptake and subcellular localization of mono-1-aspartyl chlorin e6, chloro-aluminum sulfonated phthalocyanine, and Photofrin II." Lasers Surg. Med. 1989; 9:90-101). These free radicals can disrupt cellular structures such as the cell membrane, mitochondria, and lysosomal membranes.

Visudyne® photodynamic therapy gained US marketing approval in 2000 and was approved for the treatment of patients with predominantly classic subfoveal CNV due to AMD. Visudyne therapy targets the vascular component of CNV. Its approved two-step process is one by which verteporfin, a light-activated drug (photosensitizer) delivered by intravenous (IV) infusion, is administered and then followed by nonthermal laser light application (50 J/cm$^2$ delivered at 600 mW/cm$^2$ over 83 seconds) to the CNV lesion.

Treatment of CNV using other therapies, including the use of PDT in combination with additional therapies is known in the art. Macugen® (pegaptanib) is an anti-VEGF therapy indicated in all patients with CNV due to AMD. Lucentis® (ranibizumab) is another anti-VEGF therapy indicated in all patients with CNV due to AMD (Rosenfeld P J, Brown D M, Heier J S, et al, for the MARINA Study Group. Ranibizumab for neovascular age-related macular degeneration. N Engl J. Med. 2006; 355:1419-1431; Brown D M, Kaiser P K, Michels M, et al, for the ANCHOR Study Group. Ranibizumab versus verteporfin for neovascular age-related macular degeneration. N Engl J Med. 2006; 355:1432-1444; Lucentis® (ranibizumab injection) prescribing information. San Francisco, Calif.: Genentech; 2006. http://www.gene.com/gene/products/information/tgelucentis/index.jsp. Accessed Nov. 15, 2006). The Lucentis regimen as defined in the US package insert (Lucentis® (ranibizumab injection) prescribing information. San Francisco, Calif.: Genentech; 2006. http://www.gene.com/gene/products/information/tgelucentis/index.jsp. Accessed Nov. 15, 2006) states "Lucentis 0.5 mg (0.05 mL) is recommended to be administered by intravitreal injection once a month. Although less effective, treatment may be reduced to one injection every three months after the first four injections if monthly injections are not feasible. Compared to continued monthly dosing, dosing every 3 months will lead to an approximate 5-letter (1-line) loss of visual acuity benefit, on average, over the following 9 months. Patients should be evaluated regularly."

Avastin® (bevacizumab) is an anti-VEGF monoclonal antibody that has been reported in the literature as having been used as an intravitreal injection to treat patients with CNV due to AMD, but it is not currently approved for this use. Case series of Avastin treatment for patients with AMD and other retinal diseases have been published and show an increase of mean VA in treated patients (Avery R L, Pieramici D J, Rabena M D, Castellarin A A, Nasir M A, Giust M J. Intravitreal bevacizumab (Avastin) for neovascular age-related macular degeneration, *Ophthalmology*, 2006; 113(3): 363-372; Bashshur Z F, Bazarbachi A, Schakal A, Haddad Z A, El Haibi C P, Noureddin B N. Intravitreal bevacizumab for the management of choroidal neovascularization in age-related macular degeneration. *Am J. Ophthalmol.* 2006; 142:1-9; Costa R A, Jorge R, Calucci D, Cardillo J A, Melo L A S, Scot I U. Intravitreal bevacizumab for choroidal neovascularization caused by AMD (IBeNA Study): Results of a phase I dose-escalation study. *Invest Ophthalmol Vis Sci.* 2006; 47:4569-4578; Spaide R F, Laud K, Fine H F, et al. Intravitreal bevacizumab treatment of choroidal neovascularization secondary to age-related macular degeneration, *Retina*, 2006; 26:383-390; Rich R M, Rosenfeld P J, Puliafito C A et al. Short-term safety and efficacy of intravitreal bevacizumab (Avastin) for neovascular age-related macular degeneration, *Retina*, 2006; 26:495-511).

Combination therapies using Visudyne with the intravitreal anti-VEGF therapies include Macugen (Eyetech Study Group. Anti-vascular endothelial growth factor therapy for subfoveal choroidal neovascularization secondary to age-related macular degeneration: phase II study results. *Ophthalmology* 2003; 110(5):979-986), Lucentis (Heier J S, Boyer D S, Ciulla T A, et al. Ranibizumab combined with verteporfin photodynamic therapy in neovascular age-related macular degeneration: Year 1 results of the FOCUS study. *Arch Ophthalmol.* 2006; 124:1532-1542; Schmidt-Erfurth U, Gabel P, Hohman T, Protect Study Group. Preliminary results from an open-label, multicenter, phase II study assessing the effects of same-day administration of ranibizumab (Lucentis™) and verteporfin PDT (PROTECT Study). Paper presented at: Annual Meeting of the Association for Research in Vision and Ophthalmology (ARVO); May 2, 2006; Fort Lauderdale, Fla., USA; Schmidt-Erfurth U, Gabel P, Hohman T, Protect Study Group. Preliminary results from an open-label, multicenter, phase II study assessing the effects of same-day administration of ranibizumab (Lucentis™) and verteporfin PDT (PROTECT Study). Paper presented at: Annual Meeting of the Association for Research in Vision and Ophthalmology (ARVO); May 2, 2006; Fort Lauderdale, Fla., USA; Funk M, Michels S, Wagner J, Kiss C, Sacu S, Schmidt-Erfurth U. Vascular effects of combined ranibizumab (Lucentis®) and verteporfin (Visudyne®) therapy in patients with neovascular age-related macular degeneration. Poster presented at: Annual Meeting of the Association for Research in Vision and Ophthalmology (ARVO); Apr. 30, 2006; Fort Lauderdale, Fla., USA; Wagner J, Simader C, Kiss C, Michels S, Sacu S, Schmidt-Erfurth U. Changes in functional macular mapping in patients with neovascular age-related macular degeneration receiving combination of verteporfin (Visudyne®) and ranibizumab (Lucentis™) therapy. Poster presented at Annual Meeting of the Association for Research in Vision and Ophthalmology (ARVO); Apr. 30, 2006; Fort Lauderdale, Fla., USA; Wolf S, Gabel P, Hohman T C, Schmidt-Erfurth U. Fluorescein angiographic and OCT results from an open-label, multicenter, phase II study assessing the effects of same-day ranibizumab (Lucentis™) and verteporfin PDT (Visudyne®). Paper presented at: Annual Meeting of the Association for Research in Vision and Ophthalmology (ARVO); May 3, 2006; Fort Lauderdale, Fla., USA), and Avastin (Dhalla M S, Shah G K, Blinder K J, Ryan E H Jr, Mittra R A, Tewari A. Combined photodynamic therapy with verteporfin and intravitreal bevacizumab for choroidal neovascularization in age-related macular degeneration, *Retina*, 2006; 26(9):988-993; Eter N, Ladewig M, Hamelmann V, Helb H M, Karl S, Holz F G. Combined intravitreal bevacizumab (Avastin) and photodynamic therapy for AMD. Poster presented at Annual Meeting of the American Academy of Ophthalmology (AAO), Nov. 12, 2006, Las Vegas, Nev. Abstract available at: http://www.aao.org/annual_meeting/program/onlineprogram06.cfm. Accessed on Nov. 24, 2006), have been evaluated in clinical trials and case series in subjects with AMD.

Combination therapy using Visudyne with intravitreal triamcinolone acetonide has previously been reported (Augustin A J, Schmidt-Erfurth U. Verteporfin therapy combined with intravitreal triamcinolone in all types of choroidal neovascularization due to age-related macular degeneration, *Ophthalmology*, 2006; 113(1):14-22; Spaide R F, Sorenson J, Maranan L. Combined photodynamic therapy with verteporfin and intravitreal triamcinolone acetonide for choroidal neovascularization, *Ophthalmology*, 2003; 110(8):1517-1525; Rechtman E, Danis R P, Pratt L M, Harris A. Intravitreal triamcinolone with photodynamic therapy for subfoveal choroidal neovascularisation in age related macular degeneration, *Br J. Ophthalmol.* 2004; 88(3):344-347; Van De Moere A, Sandhu S S, Kak R, Mitchell K W, Talks S J. Effect of posterior juxtascleral triamcinolone acetonide on choroidal neovascular growth after photodynamic therapy with verteporfin, *Ophthalmology*, 2005; 112(11):1897-1903; Nicolo M, Ghiglione D, Lai S, Nasciuti F, Cicinelli S, Calabria G. Occult with no classic choroidal neovascularization secondary to age-related macular degeneration treated by intravitreal triamcinolone and photodynamic therapy with verteporfin, *Retina* 2006; 26(1):58-64; Augustin A J, Schmidt-Erfuth U. Verteporfin and intravitreal triamcinolone acetonide combination therapy for occult choroidal neovascularization in age-related macular degeneration, *Am J. Ophthalmol.* 2006; 141:638-645; Ruiz-Moreno J M, Montero J A, Barile S, Zarbin M A. Photodynamic therapy and high-dose intravitreal triamcinolone to treat exudative age-related macular degeneration: 1-year outcome, *Retina*, 2006; 26:602-612). Triple therapy with Visudyne, an anti-VEGF therapy, and a steroid has also been reported (Colina-Luquez J M, Liggett P E, Tom D, Chaudhry N A, Haffner G, Cortes C F. Prospective and preliminary study evaluating triple therapy of intravitreal triamcinolone, photodynamic therapy and pegaptanib sodium for choroidal neovascularization. Poster presented at: Annual Meeting of the Association for Research in Vision and Ophthalmology (ARVO); Apr. 30, 2006; Fort Lauderdale, Fla., USA; Offermann I, Altinay A, Schmidt-Erfurth U, Augustin A J. Intravitreal bevacizumab for the treatment of remaining choroidal neovascularization (CNV) activity following combination therapy (PDT and triamcinolone). Poster presented at: Annual Meeting of the Association for Research in Vision and Ophthalmology (ARVO); May 1, 2006; Fort Lauderdale, Fla., USA; Augustin A J, Puls S, Offermann I. Triple therapy for choroidal neovascularization due to age-related macular degeneration: verteporfin PDT, bevacizumab, and dexamethasone. Retina. 2007; 27:133-140).

What is needed are additional methods of photodynamic therapy that can reduce the number of retreatments required following first treatment and that have acceptable visual acuity outcomes and acceptable safety profiles.

SUMMARY OF THE INVENTION

The present invention provides novel methods and compositions for the treatment of ocular conditions characterized by unwanted or undesired neovasculature in the eye that reduce the number of retreatments required following first treatment and that have acceptable visual acuity outcomes and acceptable safety profiles.

Accordingly in one aspect of the invention, there is provided a method for treating unwanted choroidal neovasculature (CNV) in a human subject using photodynamic therapy (PDT), the method comprising administering a photosensitizer (PS) to a subject afflicted with said neovasculature in an effective amount to permit an effective amount to localize in said ocular target tissue, and irradiating said target tissue with electromagnetic radiation containing a wavelength absorbable by said PS; and administering to the subject an effective amount of an anti-VEGF agent, wherein said administration of said anti-VEGF agent takes place in a shortened time period subsequent to the administration of the PS step, wherein closure of CNV in said subject is effected. In one embodiment, the CNV is in a subject afflicted with or diagnosed with age-related macular degeneration (AMD). In yet another embodiment, the AMD is the wet form. In other embodiments, the AMD is the predominantly classic, minimally classic, or occult form of the disease.

In one embodiment of the invention, the photosensitizer for use with the present invention comprises a green porphyrin. In other embodiments, the green porphyrin is selected from BPD-MA, BPD-DB, BPD-DA, EA6, and B3. In a preferred embodiment, the green porphyrin comprises BPD-MA. In yet another embodiment of the present invention, the PS is administered as a pharmaceutical composition. In yet other embodiments, the PS is administered as a pharmaceutical composition selected from the group consisting of a liposome, emulsion, or aqueous solution.

In another embodiment of the present invention, the anti-VEGF agent comprises an antibody for vascular endothelial growth factor. In certain embodiments, the anti-VEGF agent comprises bevacizumab or ranibizumab. In preferred embodiments, the anti-VEGF factor comprises ranibizumab. In other embodiments, the anti-VEGF agent may comprise a peptide that bind to vascular endothelial growth factor to prevent or reduce its biding to its receptor, an antibody that bind to VEGF, and a nucleic acid that can bind to VEGF, and the like.

In yet another embodiment of the present invention, the PS is irradiated with electromagnetic radiation containing a wavelength absorbed by said PS at a reduced fluence rate. In certain embodiments of the present invention, the fluence rate delivers a total light dose ranging from about 12.5 to about 25 J/cm$^2$. In a preferred embodiment, the fluence rate delivers a total light dose of about 25 J/cm$^2$ or a total light dose of 15 J/cm$^2$. In another embodiment of the invention, the fluence rate is less than about 500 mW/cm$^2$, or in other embodiments about 300 mW/cm$^2$, or in other embodiments, about 180 mW/cm$^2$.

In yet another aspect of the present invention, there is provided a method for treating unwanted choroidal neovasculature (CNV) in a human subject using photodynamic therapy (PDT), the method comprising administering a photosensitizer (PS) to a subject afflicted with said neovasculature in an effective amount to permit an effective amount to localize in said ocular target tissue, and irradiating said target tissue with electromagnetic radiation containing a wavelength absorbable by said PS; and administering to the subject an effective amount of an anti-angiogenesis factor (anti-VEGF) and an anti-inflammatory agent, wherein said administration of the anti-VEGF factor and the anti-inflammatory takes place in a shortened time period subsequent to the administration of the PS step, wherein closure of CNV in said subject is effected. In an embodiment of the invention, the anti-inflammatory agent comprises a steroid. In a preferred embodiment, the steroid comprises dexamethasone. In another embodiment of the invention, the dexamethasone is delivered intravitreally. In other embodiments, the dexamethasone is administered at a dose of between about 0.4 mg and about 0.8 mg, and within about 2 hours of administration of the PS and subsequent to administration of said anti-VEGF factor. In an embodiment of the invention, the dexamethasone is delivered at a does of about 0.5 mg.

In another aspect of the invention, the methods of the present invention are repeated for a period of about at least 6 months, or at least about 12 months following first treatment. In yet another aspect of the invention, the method is repeated about every three months for a period for about at least 6 months or more following first treatment. In other aspects of the present invention, the methods are repeated no less than about every 55 days for a period of at least 6 months following first treatment. In yet another aspect of the present invention, the methods are repeated for a period of time sufficient for visual acuity in said subject to improve.

In another aspect of the present invention, there is provided the following methods for use in improving visual acuity in a subject in need of improvement: (i) administering BPD-MA to a subject and irradiating at 300 mW/cm$^2$ for 83 seconds to deliver 25 J/cm$^2$, followed within about two hours by administration of intravitreal ranibizumab; (ii) administering BPD-MA and irradiating at 300 mW/cm$^2$ for 83 seconds to deliver 25 J/cm$^2$, followed within two hours by intravitreal ranibizumab, followed by administration of intravitreal dexamethasone; and (iii) administering BPD-MA and irradiating at 180 mW/cm$^2$ for 83 seconds to deliver 15 J/cm$^2$ followed within two hours by intravitreal ranibizumab, followed by administration of intravitreal dexamethasone. In one embodiment, the method is repeated no less than about every 55 days for a period of about 6 months or more, and wherein said visual acuity is said subject is improved. In an embodiment of the invention, the visual acuity letter score improvement from baseline after six months is at least about 2.5 letters or more. In yet another embodiment, the visual acuity letter score improvement from baseline after six months is at least about 4 letters or more, or 7 letters or more. In yet another embodiment, the visual acuity letter score improvement from baseline after twelve months is at least about 2.5 letters or more, or about 4 letters or more, or about seven letters or more.

In some embodiments, the method comprises triple combination therapy of a photosensitizer (PS) followed by an anti-VEGF agent, followed by an anti-inflammatory agent, wherein the PS is administered at a reduced fluence rate. In some embodiments, the PS is administered at about half fluence relative, for example in some embodiments at 300 mW/cm$^2$ for 83 seconds to deliver 25 J/cm$^2$, to the recommended fluence rates utilized in PDT monotherapy. In other embodiments, the PS is administered at about one quarter fluence relative, for example in some embodiments at 180 mW/cm$^2$ for 83 seconds to deliver 15 J/cm$^2$, to the recommended fluence rates utilized in PDT monotherapy. In some embodiments, the PS comprises Visudyne, the anti-VEGF agent comprises Lucentis and the anti-inflammatory comprises dexamethansone, and in some embodiments, the retreatment rate over twelve months is about 3 times, or about 4 times. In some embodiments, the treatment time between administration of Visudyne and Lucentis is about 2 hours or less than 2 hours.

In other embodiments, the method comprises double combination therapy of a photosensitizer (PS) followed by an anti-VEGF agent, wherein the PS is administered at a reduced fluence rate. In some embodiments, the PS is administered at half fluence relative, for example in some embodiments at 300 mW/cm$^2$ for 83 seconds to deliver 25 J/cm$^2$, to the recommended fluence rates utilized in PDT monotherapy. In some embodiments, the PS comprises Visudyne, the anti-VEGF agent comprises Lucentis. In some embodiments, the retreatment rate for double combination therapy over twelve months is about 4 times. In some embodiments, the treatment time between administration of Visudyne and Lucentis is about 2 hours or less than 2 hours, for example one hour or less, or 45 minutes or less, or 35 minutes or less. In other embodiments of the present invention, the retreatment rate for the combination therapy methods of the present invention are reduced relative to the number of retreatment rates for the anti-VEGF monotherapy alone without use in combination with the PS, wherein visual acuity is improved at a rate similar to that for anti-VEGF monotherapy.

In some embodiments of the present invention, the shortened time period between first administration of a PS and subsequent administration of an anti-VEGF agent is no more than about 48 hours. In other embodiments, the shortened time period is about no more than 24 hours. More preferably, the shortened time period is about no more than 4 hours, or no more than 3 hours or no more than 2 hours, or about 2 hours, or in other embodiments, less than 2 hours. In a preferred embodiment, the shortened time period comprises a period of time that allows for the subsequent treatment with an Anti-VEGF agent and, in some embodiments, an anti-inflammatory agent, during the single treatment period by the physician. In other embodiments, the shortened time period is one in which observed intraocular pressure, as monitored by techniques known to those of skill in the art, subsequent to administration of a PS is observed to be in an acceptable range and has not lead to an unacceptable increase in IOP, prior to administration of the anti-VEGF agent. Likewise, subsequent administration of an anti-inflammatory agent is administered in a time period subsequent to administration of an anti-VEGF agent, wherein intraocular pressure in the eye is observed to not have increased to unacceptable levels.

BRIEF DESCRIPTION OF THE DRAWINGS

Having thus generally described the invention, reference will now be made to the accompanying figures, showing by way of illustration preferred embodiments thereof, and in which:

FIG. 1 shows the inclusion criteria for the study of Examples 1-3 described herein;

FIG. 2 shows exclusion criteria for the study of Examples 1-3 described herein;

FIG. 3 shows the study design of Examples 1-3 described herein comparing combination therapy with ranibizumab monotherapy;

FIG. 6 shows patient baseline characteristics in the study described in Examples 1-3;

FIG. 16 shows a summary of adverse events after six months of the study as described in Examples 1-3 herein;

FIG. 17 shows a summary of ocular adverse events related to treatment after six months of the study as described in Examples 1-3 herein;

FIG. 18 shows baseline lesion composition for the different treatment groups in the study.

FIGS. 19-21 show visual acuity changes from baseline after twelve months of the study as described in Examples 1-3 herein;

FIG. 22 shows mean change from baseline of central retinal thickness after twelve months of the study as described in Examples 1-3 herein;

FIGS. 24-25 show a summary of adverse events after twelve months of the study as described in Examples 1-3 herein.

DETAILED DESCRIPTION OF THE INVENTION

Figure 4:
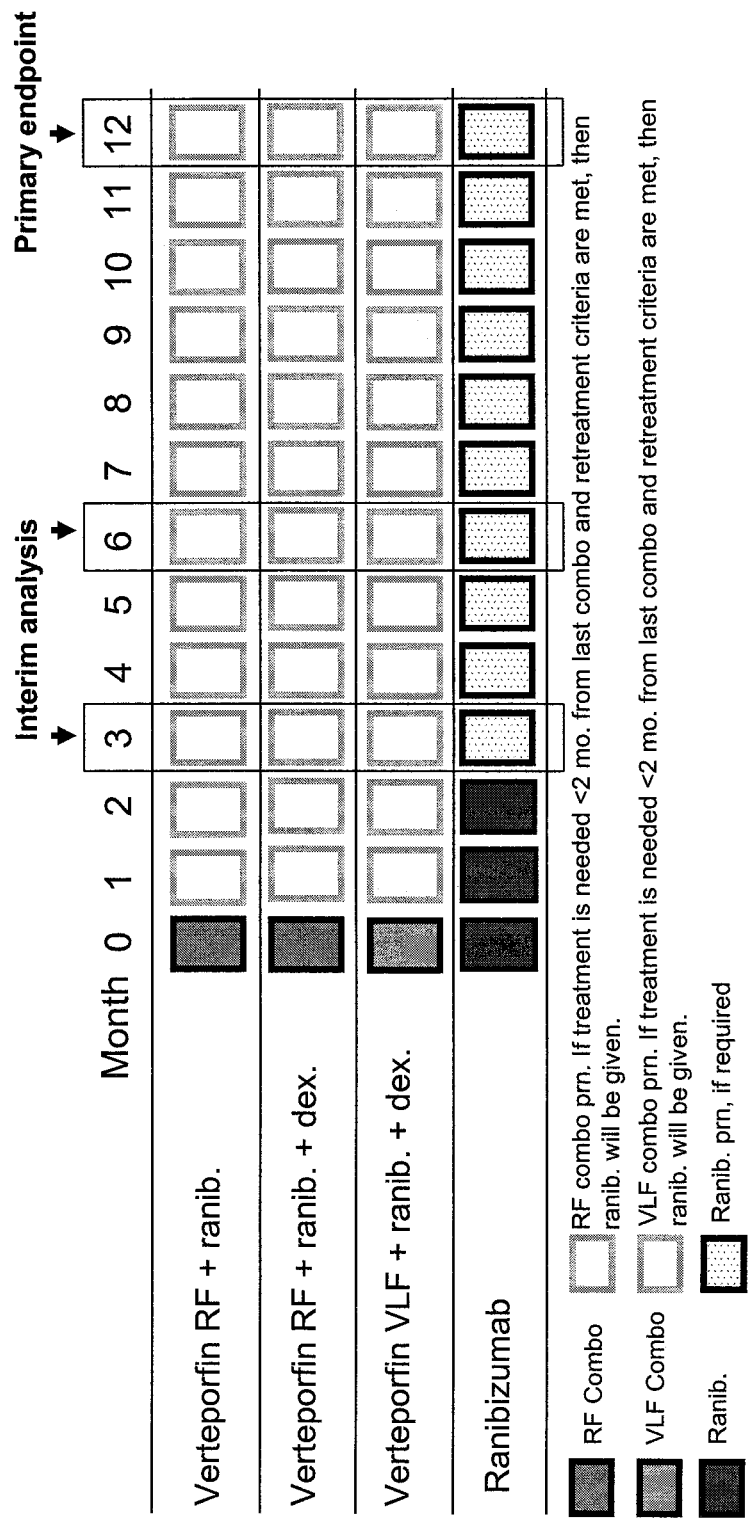
FIG. 4 shows the treatment schedule for the different treatment groups of the Study described in Examples 1-3.

Unless defined otherwise, the scientific and technological terms and nomenclature used herein have the same meaning as commonly understood by a person of skill in the art to which this invention pertains but should not be interpreted as limiting the scope of the present invention.

MODES OF CARRYING OUT THE INVENTION

In the general approach that forms the subject matter of the invention, the present invention provides novel methods and compositions for the treatment of ocular conditions characterized by unwanted or undesired neovasculature in the eye that can reduce the number of retreatments required following first treatment and that have acceptable visual acuity outcomes and acceptable safety profiles.

Photosensitizers

The invention utilizes PDT methods which generally include the administration of a photosensitizer (PS) and irradiation with a wavelength of electromagnetic radiation capable of activating the PS. The invention also includes use of a PS in the preparation of a medicament for use in any of the methods described herein.

Preferred PSs of the invention are the green porphyrins, and preferred irradiation is with visible light. A particularly preferred PS is a lipid formulation of benzoporphyrin derivative monoacid ring A, which is also known as Verteporfin or BPD-MA. Following, or simultaneous with, delivery of the PS, irradiation may be performed by any radiation source. Examples of sources of visible light radiation include operating room lamps, halogen lamps, fluorescent lamps, laser light sources, and combinations thereof. Additional examples of light sources include light emitting diode (LED) panels or flexible light diffusers which may be wrapped around a blood vessel.

As used herein "electromagnetic radiation," unless otherwise indicated, is meant generally to refer to the visible light range of the electromagnetic spectrum, generally including wavelengths between 400 nm and 700 nm. The terms "visible light" and "visible light radiation" and variations thereof are meant to be encompassed within the scope of the term "electromagnetic radiation." In addition, this term may also be used herein to refer to electromagnetic radiation within the ultraviolet (including wavelengths below 400 nm) and infrared spectra (including wavelengths above 700 nm).

Preferably, radiation, such as 690 nm light in the case of BPD-MA use, is delivered. In one embodiment, the light is from a laser, such as that capable of stably delivering 689+/−1-3 nm, and delivered to the ocular environment.

Administration of the PS may be by delivery using any appropriate means including, but not limited to, systemic, local, or even direct application to the target tissue. Local delivery of the PS provides a high local concentration while reducing the likelihood of transient skin photosensitivity or other undesirable side effects that may follow systemic PS administration. Additional suitable PSs are of a wide variety, including, without limitation, porphyrin related compounds such as hematoporphyrin derivative, Photofrin® porfimer sodium, the green porphyrins such as the BPDs, purpurins, chlorins, fluorins, etiopurpurins, and the like as well as phthalocyanines, pheophorbides, deuteroporphyrins, texaphrins, and the like.

As used herein, the term "photosensitizer," "photosensitizer compound," "photosensitizing drug," "PS," and "photoactive agent" are used interchangeably. Any variation in meaning between these terms is not meant to depart form the gist and scope of the claimed invention.

Examples of these and other PSs for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl (3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limitlavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3β-ol, nile blue derivatives, NSAIDs (non-steroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.,* 70(4):391-475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin, 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethyl-ethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-, pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1- dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate,2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo[3,2-g][1]benzopyran-2-one; 2H-selenolo[3,2-g][1]benzothiopyran-2-one; 7H-selenolo[3,2-g][1]benzoselenopyran-7-one; 7H-selenopyrano[3,2-f][1]benzofuran-7-one; 7H-selenopyrrano[3,2-f][1]benzo-thiophene-7-one; 2H-thienol[3,2-g][1]benzopyran-2-one; 7H-thienol[3,2-g][1]benzothiopyran-7-one; 7H-thiopyrano[3,2-f][1]benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2-18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminster-fullerene; [1-methyl-succinate-4-methyl-cyclohexadiene-2,3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2''3''-1:2'''3'''-q)porphyrazine; zinc (II) 2-(3-pyridyloxy)benzo[b]-10,19,28-tri(1,1-dimethylethyl)trinaphtho[2',3'-g:2''3''1::2''',3'''-q] porphyrazine; zinc(II) 2,18-bis-(3-pyridyloxy)dibenzo[b,1]-10,26-di(1,1-dimethyl-ethyl)dinaphtho[2',3'-g:2''',3'''-q] porphyrazine; zinc (II) 2,9-bis-(3-pyridyloxy)dibenzo[b,g]-17,26-di(1,1-dimethyl-ethyl)dinaphtho[2'',3''-1:2''',3'''-q] porphyrazine, zinc (II) 2,9,16-tris-(3-pyridyloxy)tribenzo[b,g,1]-24=(1,1-dimethyl-ethyl)naphtho[2''',3'''-q] porphyrazine; zinc (II) 2,3-bis-(3-pyridyloxy)benzo[b]-10,19,28-tri(1,1-dimethyl-ethyl)trinaphtho[2',3'-g:2'',3''1:2''', 3'''-q]porphyrazine; zinc (II) 2,3,18,19-tetrakis-(3-pyridyloxy)dibenzo[b,1]-10,26-di(1,1-dimethyl-ethyl) trinaphtho[2',3'-g:2'',3'''-q]porphyrazine; zinc (II) 2,3,9,10-tetrakis-(3-pyridyloxy)dibenzo[b,g]-17,26-di(1,1-dimethyl-ethyl)dinaphtho[2'',3''-1:2''',3'''-q]porphyrazine; zinc (II) 2,3, 9,10,16,17-hexakis-(3-pyridyloxy)tribenzo[b,g,1]-24-(1,1-dimethyl-ethyl)naphtho[2''',3'''-q]porphyrazine; zinc (II) 2-(3-N-methyl)pyridyloxy)benzo[b]-10,19,28-tri(1,1-dimethyl-ethyl)trinaphtho[2',3'-g:2'',3''1:2''',3'''-q]porphyrazine monoiodide; zinc (II) 2,18-bis-(3-(N-methyl)pyridyloxy) dibenzo[b,1]-10,26-di(1,1-dimethylethyl)dinaphtho[2',3'-g: 2'',3'''-q]porphyrazine diiodide; zinc (II) 2,9-bis-(3-(N-methyl)pyridyloxy)dibenzo[b,g]-17,26-di(1,1-dimethylethyl) dinaphtho[2'',3''-1:2''',3'''-q]porphyrazine diiodide; zinc (II) 2,9,16-tris-(3-(N-methyl-pyridyloxy)tribenzo[b,g,1]-24-(1,1-dimethylethyl)naphtho[2''',3'''-q]porphyrazine triiodide; zinc (II) 2,3-bis-(3-(N-methyl)pyridyloxy)benzo[b]-10,19,28-tri(1,1-dimethylethyl)trinaphtho[2',3'-g:2'',3''-1:2''',3'''-q]

porphyrazine diiodide; zinc (II) 2,3,18,19-tetrakis-(3-(N-methyl)pyridyloxy)dibenzo[b,1]-10,26-di(1,1-dimethyl) dinaphtho[2',3'-g:2''',3'''-q]porphyrazine tetraiodide; zinc (II) 2,3,9,10-tetrakis-(3-(N-methyl)pyridyloxy)dibenzo[g,g]-17, 26-di(1,1-dimethylethyl)dinaphtho[2'',3''-1:2''',3'''-q]porphyrazine tetraiodide; zinc (II) 2,3,9,10,16,17-hexakis-(3-(N-methyl)pyridyloxy)tribenzo[b,g,1]-24-(1,1-dimethylethyl)naphtho[2''',3'''-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)-3-phthalocyanato palladium (II); ruthenium(II) dipotassium[bis(triphenyl-phosphine-monosulphonate) phthalocyanine; silicon phthalocyanine bis (tri-n-hexyl-siloxy)-; silicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2N(CH_3)_2]_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22, 25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17, 23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 µM); methylene blue (14 µM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide, N,N'-bis(2,2-dimethoxyethyl)-1,4,5,8-naphthaldiimide, and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecylsiloxy)naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine, silicon bis(tert-butyldimethylsiloxy) naphthalocyanine; silicon bis(tri-n-hexylsiloxy) 2,3-naphthalocyanine; silicon bis(tri-n-hexylsiloxy)naphthalocyanine; silicon naphthalocyanine; t-butylnaphthalocyanine; zinc (II) naphthalocyanine; zinc (II) tetraacetyl-amidonaphthalocyanine; zinc (II) tetraminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl)propionic acid); carprofen (3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol]hypocrellin B; 3,10-bis[4-(2-aminoethyl)morpholine]hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)]hypocrellin B; 5,8-dibromo[1,12-CHBrC(=CH$_2$)CBr(COMe)]hypocrellin B; 5,8-dibromo[1-CH$_2$COMe, 12-COCOCH$_2$Br—]hypocrellin B; 5,8-dichloro hypocrellin A; 5,8-dichloro hypocrellin B; dichlorodeacytylated hypocrellin B; 5,8-diiodo hypocrellin A; 5,8-diiodo hypocrellin B; 5,8-diiodo[1,12-CH=CMeCH(COCH$_2$I$_2$)-] hypocrellin B; 5,8-diiodo[1,12-CH$_2$C(CH$_2$I)=C(COMe)-] hypocrellin B; 2-(N,N-diethylamino)ethylaminated hypocrellin B; 3,10-bis[2-(N,N-diethylamino)-ethylamine] hypocrellin B; 4,9-bis[2-(N,N-diethyl-amino)-ethylamine] iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)-]hypocrellin B; 8-iodo[1,12-CH$_2$C(CH$_2$I)=C(COMe)-]hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-(2$^3$-carboxy-2$^4$-methoxycarbonyl benzo)-7,12,17-tris(2-methoxyethyl)porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy)porphycene; 2,7,12,17-tetrakis(2- methoxyethyl)-9-[4-((β-apo-7-carotenyl)benzoyloxy]-porphycene; 2,7,12,17-tetrakis(2-methoxyethyl)-9-aminoporphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6,13,16-dibenzo-porphycene; 2,7-bis(2-hydroxyethyl)-12,17-di-n-propyl-porphycene; 2,7-bis(2-methoxyethyl)-12,17-di-n-propyl-porphycene, and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra (o-hydroxyphenyl)porphyrin; 5,10,15,20-tetra(m-hydroxyphenyl)porphyrin; 5,10,15,20-tetrakis-(m-hydroxyphenyl) porphyrin; 5,10,15,20-tetra(p-hydroxyphenyl)porphyrin; 5,10,15,20-tetrakis(3-methoxyphenyl)porphyrin; 5,10,15,20-tetrakis(3,4-dimethoxyphenyl)porphyrin; 5,10,15,20-tetrakis(3,5-dimethoxyphenyl)porphyrin; 5,10,15,20-tetrakis(3,4,5-trimethoxyphenyl)porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18, 23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N"-trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl)porphine; tetraphenylporphyrin sulfonate; meso-tetra(4-sulfonatophenyl)porphine; tetrakis(4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl) porphyrin; meso-tetra(4-N-trimethylanilinium)-porphine; uroporphyrin; uroporphyrin I (17 μM); uroporphyrin IX; and uroporphyrin I (18 μM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2': 5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'"-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1'", 1'"-dibromoethenyl)-2,2':5',2"-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',2"-terthiophene; 5-(3'",3'"-dimethylacryloyloxymethyl)-2,2':5',2"-terthiophene, 5,5"-di-(t-butyl)-2,2':5',2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3'"-methyl-2'"-butenyl)-2,2':5',2"-terthiophene; methyl 2,2':5',2"-terthiophene-5-[3'"-acrylate]; methyl 2,2':5',2"-terthiophene-5-(3'"-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene derivative, and miscellaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5',":5",2'"-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methylpyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion)methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodofluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester, rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, his (triethyl-ammonium salt); rose bengal his (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Particularly preferred PSs are the green porphyrins, such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Other photosensitizers that may be used in the present invention include those described in U.S. Pat. Nos. 5,308,608, 6,093,739, 5,703,230, 5,831,088, 5,726,304, and 5,405,957. Of course, combinations of photosensitizers may also be used. It is preferred that the absorption spectrum of the photo sensitizer be in the visible range, typically between 350 nm and 1200 nm, more preferably between 400-900 nm, and even more preferably between 600-900 nm.

BPD-MA is described, for example, in U.S. Pat. No. 5,171, 749; EA6 and B3 are described in U.S. Ser. Nos. 09/088,524 and 08/918,840, respectively, all of which are incorporated herein by reference. Preferred green porphyrins have the basic structure:

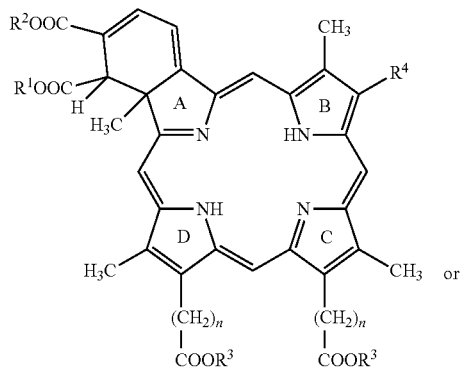

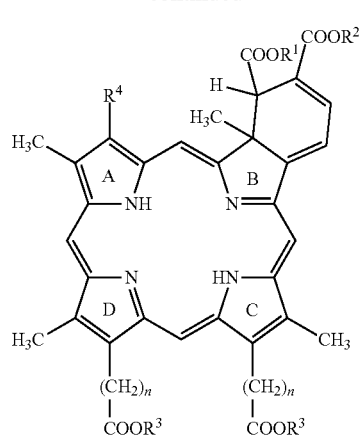

2

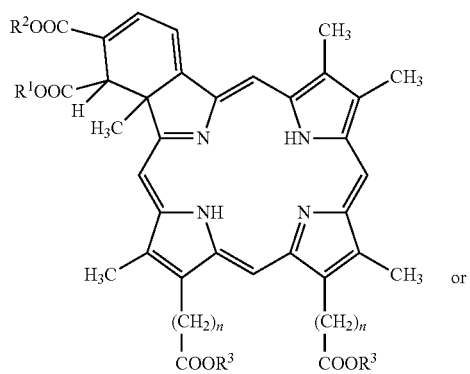

3

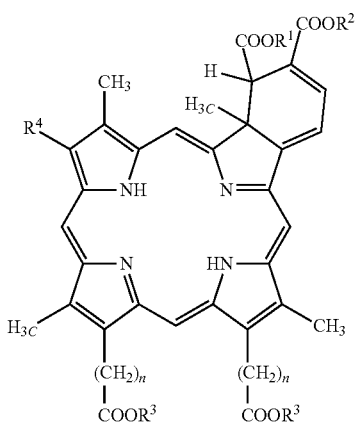

4 where R⁴ is vinyl or 1-hydroxyethyl and R¹, R², and R³ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin, as well as illustrations of A and B ring forms of EA6 and B3, are as follows:

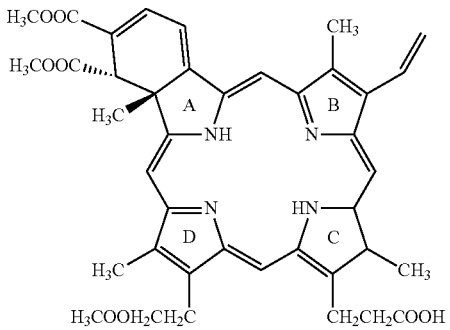

BPD-MA$_C$

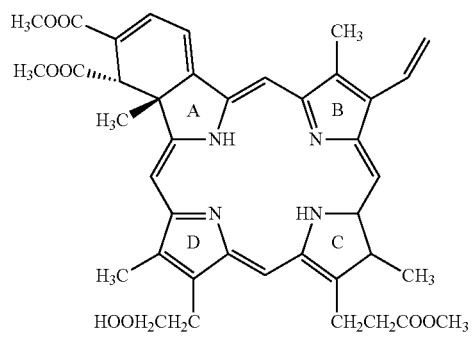

BPD-MA$_D$

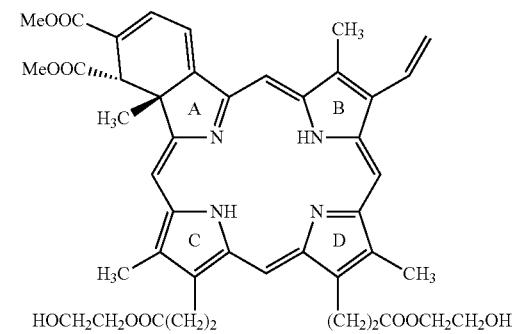

A-EA6

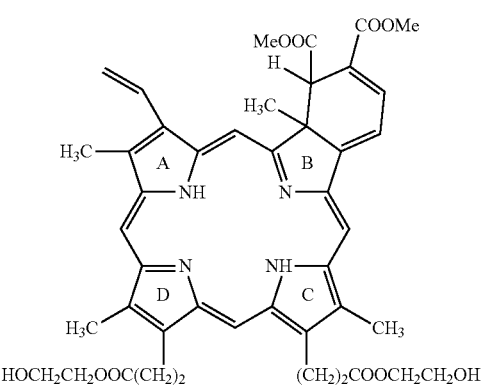

B-EA6

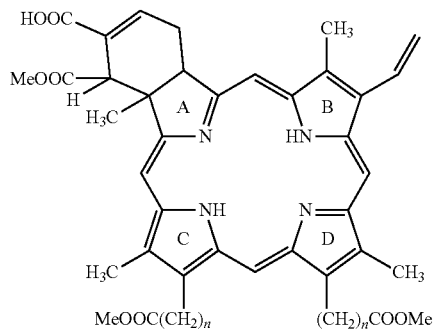

A-B3

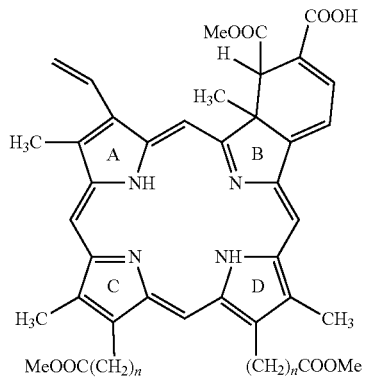

B-B3

Related compounds of formulas 3 and 4 are also useful; in general, $R^4$ will be vinyl or 1-hydroxyethyl and $R^1$, $R^2$, and $R^3$ are H or alkyl or substituted alkyl.

Light Treatment

The irradiation levels will be in the range generally employed for PDT treatment of CNV as known in the art. Typical levels for the practice of the invention are in the range of about 12.5, 25, 50, 75, and 100 J/cm². The radiation can be supplied by any convenient source using a wavelength absorbed by the PS used. Examples of sources for use in the present methods include any assembly capable of producing visible light.

PS spectra, as well as wavelengths for PS activation, have been described in the art. Irradiation of the administered PS is preferably at the wavelength absorbed by the PS selected. For any particular PS, it is a trivial matter to ascertain the spectrum. For green porphyrins, however, the desired wavelength range is generally between about 550 and 695 nm. Preferred wavelengths for the practice of the invention are at about 685-695 nm, particularly at about 686, about 687, about 688, about 689, about 690, about 691, and about 692 nm.

Throughout this disclosure, the shortened term "reduced fluence rate" is used to mean "reduced rate of applied light dose achieved by reduced fluence rate." Preferably, the reduced fluence rates of the invention result in better selectivity to the CNV as well as decrease closure of normal choriocapillaris and other unwanted or undesirable damage to normal tissue at or near the treated CNV. Because standard, higher, light fluence rates may lead to hypoxia, angiogenesis stimulation, further CNV growth, and possibly reductions of the duration of the therapeutic benefit, the reduced fluence rates for use with the present invention may avoid these possibilities by decreasing the likelihood of depleting molecular oxygen levels at the site of PDT. Without being bound by theory, it is hypothesized that a reduced light fluence rate will result in a more selective treatment benefit compared to controls using a higher fluence rate.

In preferred embodiments of the invention, the subject to be treated is human, and the site of CNV is in the eye. In particularly preferred embodiments, the human subject is afflicted with the "wet" form of age-related macular degeneration (AMD). In other preferred embodiments of the invention, the irradiation step is with light containing wavelengths in the visible range.

As used herein, "photodynamic productivity" or "photodynamic product" is meant to refer to the reaction product caused by the interaction of PS with electromagnetic radiation and molecular oxygen.

In the present invention, PDT with a reduced fluence rate may be used to treat CNV in a subject afflicted or diagnosed therewith. PDT is basically conducted via conventional means, wherein the subject is administered a suitable PS compound in amount sufficient to provide an effective concentration of the PS at the site of the CNV. After a suitable time period to permit an effective concentration of the PS to accumulate, the region to be treated is irradiated (or illuminated or otherwise activated) with electromagnetic radiation containing one or more wavelengths which activate the PS. In a preferred embodiment of the present invention, double combination therapies utilizing a PS and an anti-VEGF agent are conducted at reduced fluence, preferably at about half fluence relative to standard fluence. In some embodiments, reduced fluence comprises 25 J/cm². In other embodiments, triple combination therapies utilizing a PS and an anti-VEGF agent and an anti-inflammatory are conducted at reduced fluence, preferably at about half fluence or about one quarter fluence relative to standard fluence. In some embodiments, reduced fluence for triple combination therapy comprises 25 J/cm² or 15 J/cm².

The light dose (fluence) associated with standard verteporfin PDT is 50 J/cm², administered at intensity (fluence rate) of 600 mW/cm² for 83 seconds. Reducing the fluence (light dose) can be achieved by reducing the fluence rate (light intensity) or by reducing the time of light administration. As disclosed herein, reduced fluence rates are preferred for the practice of the invention for both double and triple combination therapy using a PS. Reduced fluence rates should not be confused with total PDT dose, which is generally described as the combination of the concentration of the photosensitizing drug, the intensity of the radiation employed and the time of exposure to light, which determines the total amount of energy ultimately delivered to the target tissue. The fluence rate is but one part of the total PDT dose and as such may be changed with or without affecting the total PDT dose depending on the time of light exposure. For example, if the fluence rate is reduced and the time kept constant, a lower total PDT dose is provided. Alternatively, if the fluence rate is reduced and the time of exposure increased, the same total PDT dose can be provided. Reduced fluence rates have the additional advantage of decreasing the likelihood of hyperthermic and other damaging effects. Methods for conducting reduced fluence PDT are taught in U.S. Pat. No. 6,800,086, the entire contents of which are incorporated herein by reference.

It is understood that the selection of particular fluence rates will vary according to the nature of the neovasculature and tissue being treated and the nature of the PS employed. However, the conditions for PDT (including PS concentration, fluence rate, and time of irradiation) cannot vary over any arbitrary range. There are actual constraints which are known by the skilled practitioner with the use of any PS in PDT. Preferred rates for use with green porphyrins or BPDs is from about 180 to 250, about 250 to 300, about 300 to 350, about 350 to 400, about 400 to 450, about 450 to 500, and about 500 to 550 mW/cm$^2$. Particularly preferred is a fluence rate of 180 or 300 mW/cm$^2$.

As indicated above, the total PDT dose depends on the balance of at least the concentration of PS employed, light intensity (fluence rate), and time of irradiation which determines total energy. The values set forth herein below for these parameters indicates the range in which they may be varied; however, equivalents of the following are known to the skilled practitioner and are also within the scope of the invention.

Treatments in accordance with the present invention can be repeated. For example, and without limiting the invention, treatments may be repeated at approximately every fifty-fifth day (approximately about every 2 month) intervals or approximately every three months (+/−2 weeks) if CNV leakage is found to continue or as deemed necessary by the skilled practitioner. In one embodiment, the invention provides for reevaluation of the patient for recurring neovascular leakage at least twice within a period of six months of the first treatment, and if neovascular leakage has occurred, the patient is retreated with the methods of the present invention. In preferred embodiments of the invention, the procedure is repeated at least once, or at least twice or at least three times within about 6 months from the first treatment. The invention provides an improved method of treatment by providing for less treatments during the first six months following initial treatment.

Treatment efficacy can be evaluated by a number of different protocols, including, but not limited to fluorescein angiography (FA) to determine the area of CNV leakage and optical coherence tomography (OCT). Closure of choroidal neovascularization may also be confirmed histologically by the observation of damage to endothelial cells. Observations to detect vacuolated cytoplasm and abnormal nuclei associated with disruption of neovascular tissue may also be evaluated.

Of particular importance with respect to the present invention is the evaluation of visual acuity. This is done using means standard in the art and conventional "eye charts" in which visual acuity is evaluated by the ability to discern letters of a certain size, usually with five letters on a line of given size. Measures of visual acuity are known in the art and standard means are used to evaluate visual acuity according to the present invention.

PS Concentrations

The PS concentration in the formulation to be administered will depend on the nature of the tissue to be treated, the manner in which the formulation is administered, and the nature of the PS. Typical concentrations, however, are in the range of about 1 ng/ml to about 10 µg/ml, preferably about 2 ng/ml to about 1 µg/ml, and typically in the range of about 10 ng/ml to about 100 ng/ml. However, these values are merely suggestions and may not apply to all PSs. For localized application of BPD-MA and other green porphyrins or porphyrin derivatives (especially those listed above), a range of about 0.01 to about 0.2 or about 0.5 mg/ml is contemplated. Preferably, about 0.075 mg/ml is used. For systemic application of PS, the range may be about 2-8 (or more preferably 6) mg/m2 (BPD-MA/body surface area). 6 mg/m2 is approximately 0.15 mg/kg. In a preferred embodiment, the PS comprises commercially available Visudyne® (verteporfin for injection).

Systemic administration can also be stated in terms of amount of PS to body weight of the subject being treated. Dosages for this invention stated in such terms are less than about 10 µg/kg to 100 mg/kg body weight, preferably less than about 10 mg/kg, more preferably about 0.15 mg/kg in humans. Preferably, the PS is infused into a subject over a short period, such as, but not limited to, about 5 to about 120 minutes, about 10 to about 90 minutes, about 20 to about 60 minutes, or about 30 to 45 minutes. Particularly preferred is an infusion over 10 minutes.

In embodiments of the present invention, verteporfin PDT is administered with reduced fluence in all three combination therapy arms of the study set out in the Examples below. The reduced light dose is achieved by reducing the fluence rate. In two arms (double therapy and one triple therapy arm), half fluence (25 J/cm2) is administered (300 mW/m2 for 83 seconds), and in the remaining triple therapy arm, very low fluence (15 J/cm2) is given (180 mW/m2 for 83 seconds).

Photosensitizer Formulations

In applications of the present invention to the treatment of ocular neovasculature, the photoactive agent is preferably formulated so as to deliver an effective concentration to the target ocular tissue. The photoactive agent may be coupled to a specific binding ligand which may bind to a specific surface component of the target ocular tissue or, if desired, by formulation with a carrier that delivers higher concentrations to the target tissue. The formulation may be a liposomal formulation, an emulsion, or simply an aqueous solution. Buffers and other excipients may also be added. Gelling agents and other excipients may also be employed.

The nature of the formulation will depend in part on the mode of administration and on the nature of the photoactive agent selected. To prepare a pharmaceutical formulation or composition comprising a PS of the invention, any pharmaceutically acceptable excipient, or combination thereof, appropriate to the particular photoactive compound may be used. Thus, the photoactive compound may be administered as an aqueous composition, as a transmucosal or transdermal composition, or in an oral formulation. Liposomal compositions are particularly preferred especially where the photoactive agent is a green porphyrin. Liposomal formulations are believed to deliver the green porphyrin selectively to the low-density lipoprotein component of plasma which, in turn acts as a carrier to deliver the active ingredient more effectively to the desired site. Increased numbers of LDL receptors have been shown to be associated with neovascularization, and by increasing the partitioning of the green porphyrin into the lipoprotein phase of the blood, it appears to be delivered more efficiently to neovasculature.

The optimum time following PS administration until light treatment can also vary widely depending on the mode of administration, the form of administration and the specific ocular tissue being targeted. Typical times after administration of the photoactive agent range from about 1 minute to about 2 hours, preferably about 5-30 minutes, and more preferably about 10-25 minutes. Particularly preferred is irradiation at 15 minutes after the start of PS infusion. The incubation before irradiation may occur in the dark or low-level light may be supplied during PS administration.

Anti-VEGF Agents

The invention utilizes anti-VEGF agents in combination therapy. Preferred anti-VEGF factors include antibodies, peptides and nucleic acids that can bind to vascular endothelial growth factor to prevent or reduce its binding to its receptor. Preferred anti-VEGF agents for use with the present invention are antibodies for vascular endothelial growth factor receptor (VEGF-2R). As used herein, antibodies for use with the present invention include monoclonal antibodies, polyclonal antibodies, and antigen binding fragments thereof. Anti-VEGF agents can be administered at dosing ranges, for example, from about 0.01 to about 500 mg/kg, more preferably from about 0.01 to about 250 mg/kg. Antibodies that bind to VEGF may be administered intravenously, more preferably as a bolus, at doses ranging from about 5 µg to about 5 mg/eye. Preferred anti-VEGF agents include ranibizumab and bevacizumab.

In embodiments of the present invention, the time period between first administration of a PS and subsequent administration of an anti-VEG agent can vary. Typical time period are no more than about 48 hours. In other embodiments, a typical time period comprises a shortened time period is about no more than 24 hours. More preferably, the shortened time period is about no more than about 4 hours, or no more than about 3 hours or no more than about 2 hours, or about 2 hours, or in other embodiments, less than about 2 hours, for example less than 60 minutes, or less than 45 minutes or between about 15-60 minutes, or between about 15-45 minutes, or between about 15 and 35 minutes. In a preferred embodiment, the shortened time period comprises a period of time that allows for the subsequent treatment with an Anti-VEGF agent and, in some embodiments, an anti-inflammatory agent, during the single visit to the treating physician. In other embodiments, the shortened time period is one in which observed intraocular pressure, as monitored by techniques known to those of skill in the art, subsequent to administration of a PS is observed to be in an acceptable range and has not lead to an unacceptable increase in IOP, prior to administration of the anti-VEGF agent.

Anti-Inflammatory Agents

Methods of the present invention may be further enhanced by the use of combining PDT and anti-VEGF agents with an anti-inflammatory agent. An anti-inflammatory agent can be any agent that counteracts or suppresses the inflammatory process. Anti-inflammatory agents for use with the present invention include steroidal and non-steroidal agents. Preferably, the anti-inflammatory is administered subsequent to the administration of the PS. Preferably, the anti-inflammatory agent comprises a steroid, such as dexamethasone. The steroid may be administered intravitreally, although other routes of administration may also be utilized, including as directed and in dosages as described in the respective package inserts and as described herein, when using a commercially available anti-inflammatory agent. In other embodiments, the dexamethasone may be administered at a dose of between about 0.4 mg and about 0.8 mg, and within about 2 hours of administration of the PS and subsequent to administration of said anti-VEGF factor. In an embodiment of the invention, the dexamethasone is delivered at a does of about 0.5 mg. In some embodiments, administration of an anti-inflammatory agent is administered in a time period subsequent to administration of an anti-VEGF agent, wherein intraocular pressure in the eye is observed to not have increased to unacceptable levels.

Without wishing to be bound to any particular theory, the rationale for combination therapy in choroidal neovascularization (CNV) due to AMD has been described (Augustin A J, Offerman I. Combination therapy for choroidal neovascularisation. *Drugs Aging* 2007; 24(12):979-990; Kaiser, P. Verteporfin photodynamic therapy and anti-angiogenic drugs: potential for combination therapy in exudative age-related macular degeneration. *Curr Med Res Opin.* 2007; 23(3):477-487; Spaide R F. Rationale for combination therapies for choroidal neovascularization. *Am J Ophthalmol* 2006; 141: 149-156) and is fundamentally the same as the combination therapy rationale in oncology. In combination therapy, each treatment component has a different mechanism of action, so combining treatment components attacks the diseased area in different ways. The development of CNV due to AMD is complex and poorly understood, but is believed to involve inflammation, angiogenesis, and neovascularization. In combination therapies of the present invention, PDT with a PS, e.g., Visudyne, is thought to occludes existing neovascularization, the anti-vascular endothelial growth factor (anti-VEGF) therapy, e.g. ranibizumab, is believed to stop angiogenesis and reduce leakage, and the anti-inflammatory, e.g., dexamethasone, is applied to fight inflammation. It is believed that such a multi-component, multi-target approach to therapy may result in acceptable vision outcomes that last longer than outcomes associated with ranibizumab monotherapy, which currently is approved for administration monthly to maintain the best vision benefit (Rosenfeld P J, Brown D M, Heier J S, et al, for the MARINA Study Group. Ranibizumab for neovascular age-related macular degeneration. *N Engl J. Med.* 2006; 355:1419-1431; Brown D M, Kaiser P K, Michels M, et al, for the ANCHOR Study Group. Ranibizumab versus verteporfin for neovascular age-related macular degeneration. *N Engl J. Med.* 2006; 355:1432-1444; Lucentis® (ranibizumab injection) prescribing information. San Francisco, Calif.: Genentech; 2006. http://www.gene.com/gene/products/information/tgr/lucentis/index.jsp. Accessed Nov. 15, 2006).

Longer-lasting outcomes could result fewer re-treatments, which would lessen the burden of frequent clinic visits for patients, free retinal specialists to treat more patients, and lower the cost of treatment for both patients and the entities that pay for health care.

The following examples are meant to illustrate but not limit the invention.

Example 1

Study Design

The study is a 24-month randomized, controlled trial designed to evaluate 3 combination treatment regimens: (1) very low-fluence vPDT (15 J/cm$^2$) combined with ranibizumab (0.5 mg) and dexamethasone (0.5 mg); (2) half-fluence vPDT (25 J/cm$^2$) combined with ranibizumab and dexamethasone; and (3) half-fluence vPDT combined with ranibizumab. These regimens are compared with ranibizumab monotherapy in patients with subfoveal choroidal neovascularization (CNV) due to AMD. Inclusion criteria includes ≥50 years old; naïve to AMD treatment; best-corrected VA (BCVA) letter score of 73-24; subfoveal CNV due to AMD; and lesion size <9 DA. Patients (N=160) are randomly assigned to 1 of the 4 treatment arms at baseline, receive 1 initial treatment, and are to be evaluated for retreatment every month based on novel criteria using OCT and FA. Patients in the ranibizumab monotherapy group receive mandatory dosing at months 1 and 2, and as needed thereafter based on the same retreatment criteria. Patients in the combination therapy groups receive assigned treatment as needed (not more frequently than every 2 months), based on retreatment criteria; if treatment is required in an intervening month, then a ranibizumab injection is given. Study outcomes include efficacy, safety, and number of retreatments.

After their initial randomized study treatment, patients in the combination therapy groups return to the clinic monthly for re-treatment evaluation. Re-treatment criteria are based on optical coherence tomography (OCT) and fluorescein angiography (FA). If OCT central retinal thickness (CRT) is ≥250 µm or is increased >50 µm compared with the lowest previous CRT measurement, then the patient is re-treated. If neither OCT criteria applies, the patient may still be re-treated if FA shows evidence of lesion growth or leakage from CNV.

Combination re-treatment is not administered more frequently than every 2 months. If re-treatment is found to be needed in an intervening month, the patient receives a ranibizumab injection only. After their initial randomized study treatment, patients in the ranibizumab monotherapy group receive mandatory re-treatment at months 1 and 2, and then re-treatment as needed thereafter based on the criteria described above. In all treatment arms, monthly assessments and potential re-treatments continue through 12 months of the study. Between 12 and 24 months, patients attend the clinic at least once every 3 months, or more frequently at the investigator's discretion.

Best-corrected visual acuity is assessed by the ETDRS method at screening, on the day of initial treatment (before treatment), at monthly visits through 6 months, and at the 12-, 18-, and 24-month visits. FA is assessed at screening, at the 3- and 12-month visits, and as required according to re-treatment criteria. OCT is assessed to determine retreatment criteria at every visit. Safety, including intraocular pressure, is also evaluated at every visit.

Study outcomes include visual acuity, CRT, lesion size, number of re-treatments, and safety. The primary efficacy variables are mean number of re-treatments and mean change from baseline in visual acuity score.

Example 2

Materials and Methods

Dexamethasone Sodium Phosphate Injection, USP 10 mg/mL in 1 mL is used in the study. (Baxter Healthcare Corporation, Deerfield, Ill., USA or Sandoz Canada Inc.) Each milliliter contains dexamethasone sodium phosphate equivalent to 10 mg dexamethasone phosphate or 8.33 mg dexamethasone. The inactive ingredients in this formulation are sodium sulfite anhydrous, sodium citrate anhydrous, and benzyl alcohol (preservative) in Water for Injection.

Randomization occurs on the day of the first treatment to one of the following groups:
  Lucentis monotherapy.
  Half-fluence Visudyne-Lucentis (V-L) double therapy.
  Half-fluence (25 J/cm$^2$) Visudyne-Lucentis-Dexamethasone (V-L-D) triple therapy.
  Very low-fluence (15 J/cm$^2$) Visudyne-Lucentis-Dexamethasone (V-L-D) triple therapy.

Treatments occur within 7 days of baseline FA. Retreatment is according to retreatment criteria in the Lucentis monotherapy group starting at Month 3 and in the combination therapy groups starting at Month 1. All retreatment procedures are completed on the same day, if possible (i.e., evaluation of OCT and FA, and retreatment, if needed). If this is not possible, retreatment, if needed, is recommended to be completed within 3 days of OCT.

Lucentis (ranibizumab) is administered as described in the approved prescribing information.

Reconstituted Visudyne is an opaque dark green solution. The volume of reconstituted Visudyne required to achieve the desired dose of 6 mg/m$^2$ body surface area (BSA) is withdrawn from the vial and diluted with dextrose 5% in water (D5W) to a total infusion volume of 30 mL. The full infusion volume is administered intravenously over 10 minutes at a rate of 3 mL/minute, using an appropriate syringe pump and in-line filter (1.2 micron).

Light application to the study eye is performed 15 minutes after the start of infusion of Visudyne. Light is administered as follows, depending on the treatment to which the subject is assigned:

Visudyne-Lucentis double therapy and half-fluence V-L-D triple therapy groups: The light dose of 25 J/cm$^2$ is delivered over 83 seconds at a light fluence rate of 300 mW/cm$^2$.

Very low-fluence V-L-D triple therapy group: The light dose of 15 J/cm$^2$ is delivered over 83 seconds at a light fluence rate of 180 mW/cm$^2$. For this regimen, the minimum treatment spot size is 3.8 mm (required to achieve this light dose with the laser systems available).

Red light (689±3 nm) produced by a diode laser is delivered to the CNV lesion as a single circular spot through a fiber optic and a slit lamp using a suitable contact lens.

The size of the CNV lesion is estimated from the fluorescein angiograms that delineate the CNV and any features that block the boundaries of any CNV.

For the V-L-D therapy group assigned to 15 J/cm$^2$, the minimum treatment spot size is 3.8 mm, so the border for lesions with a GLD smaller than 2.8 mm will be proportionally greater than the 500 micron border stated above.

The dexamethasone injection is administered aseptically, as described for Lucentis. A 29- or 30-gauge needle will be used to administer each drug.

Example 3

Study Results

Groups of patients who had been diagnosed as qualified for experimental treatment of age related macular degeneration in the study set out in Example 1 and 2 above were divided into four groups as shown in FIGS. 1-3, 18 and treated with one of four regimens as set out in FIG. 4 as follows:
  Lucentis 0.5 mg monotherapy:
    Day 0, Month 1, and Month 2
    PRN (based on retreatment criteria) with monthly assessments Months 3-12
    PRN (based on retreatment criteria) to Month 21, with assessments at least every 3 months after Month 12 to Month 24
    All Lucentis injections must be ≥28 days apart
  Visudyne-Lucentis double therapy with half-fluence (25 J/cm$^2$: 300 mW/cm$^2$ for 83 seconds) Visudyne followed within 2 hours by intravitreal Lucentis 0.5 mg:
    Day 0
    Assessments monthly to Month 12. Double therapy will be given PRN (based on retreatment criteria), but at no less than 2-month (55-day) intervals. If treatment is needed in an intervening month, based on retreatment criteria, then subjects will receive a Lucentis injection (as long as it has been ≥28 days since the previous Lucentis injection).
    Assessments at least every 3 months after Month 12 to Month 24. Treatment PRN to Month 21 as described above.
  V-L-D triple therapy with half-fluence (25 J/cm$^2$: 300 mW/cm$^2$ for 83 seconds) Visudyne followed within 2 hours by intravitreal Lucentis 0.5 mg (first injection) and intravitreal dexamethasone 0.5 mg (second injection):
    Day 0
    Assessments monthly to Month 12. Half-fluence triple therapy will be given PRN (based on retreatment criteria), but at no less than 2-month (55-day) intervals. If treatment is needed in an intervening month, based on retreatment criteria, then subjects will receive a Lucentis injection (as long as it has been ≥28 days since the previous Lucentis injection).

Assessments at least every 3 months after Month 12 to Month 24. Treatment PRN to Month 21 as described above.

V-L-D triple therapy with very low-fluence (15 J/cm$^2$: 180 mW/cm$^2$ for 83 seconds) Visudyne followed within 2 hours by intravitreal Lucentis 0.5 mg (first injection) and intravitreal dexamethasone 0.5 mg (second injection):

Day 0

Assessments monthly to Month 12. Very low-fluence triple therapy will be given PRN (based on retreatment criteria), but at no less than 2-month (55-day) intervals. If treatment is needed in an intervening month, based on retreatment criteria, then subjects will receive a Lucentis injection (as long as it has been ≥28 days since the previous Lucentis injection).

Assessments at least every 3 months after Month 12 to Month 24. Treatment PRN to Month 21 as described above.

Figure 5:
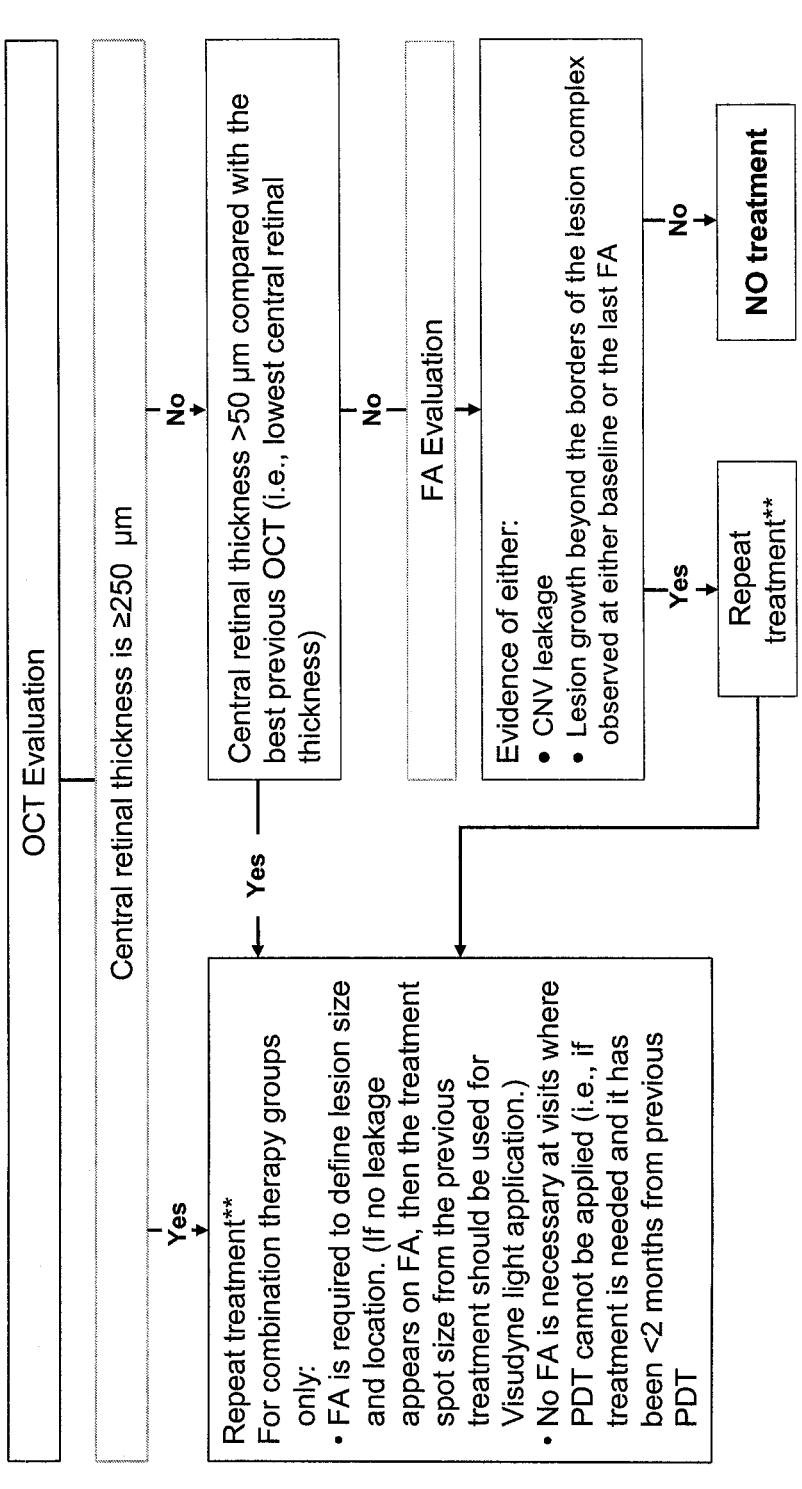
FIG. 5 shows the retreatment criteria employed in the study described in Examples 1-3.
Figure 7:
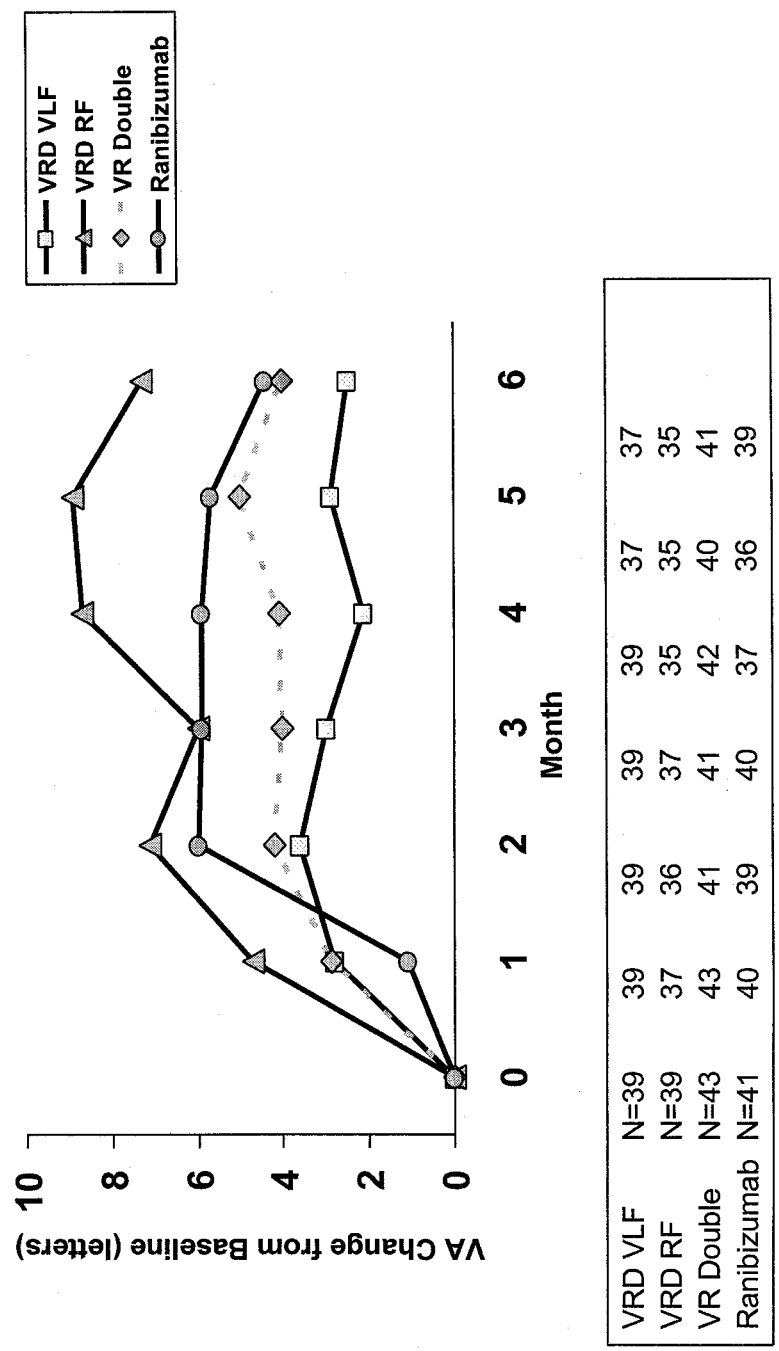
FIGS. 7-10 show mean visual acuity change from baseline after six months of the study as described in Examples 1-3 herein.
Figure 8:
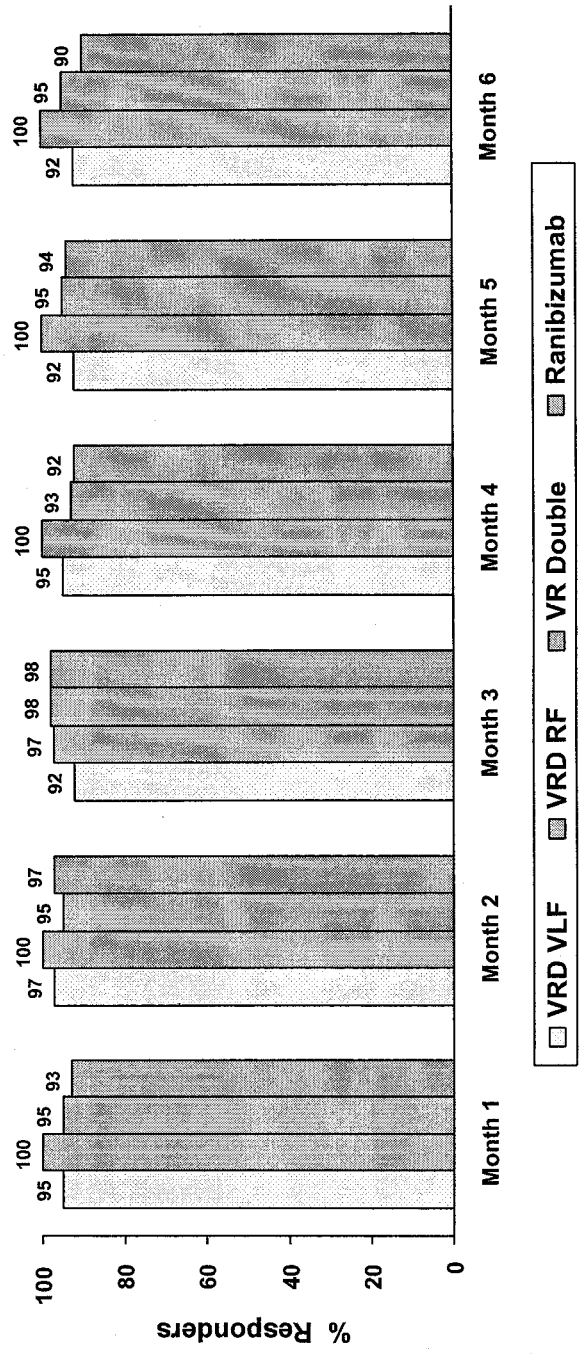
Figure 9:
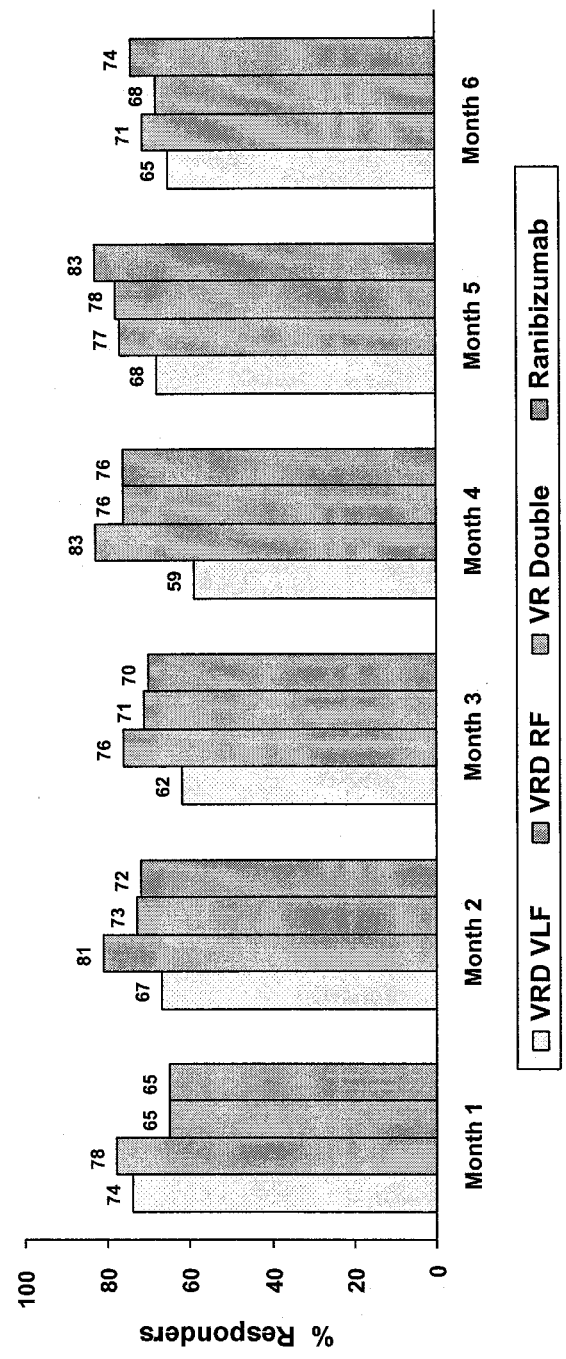
Figure 10:
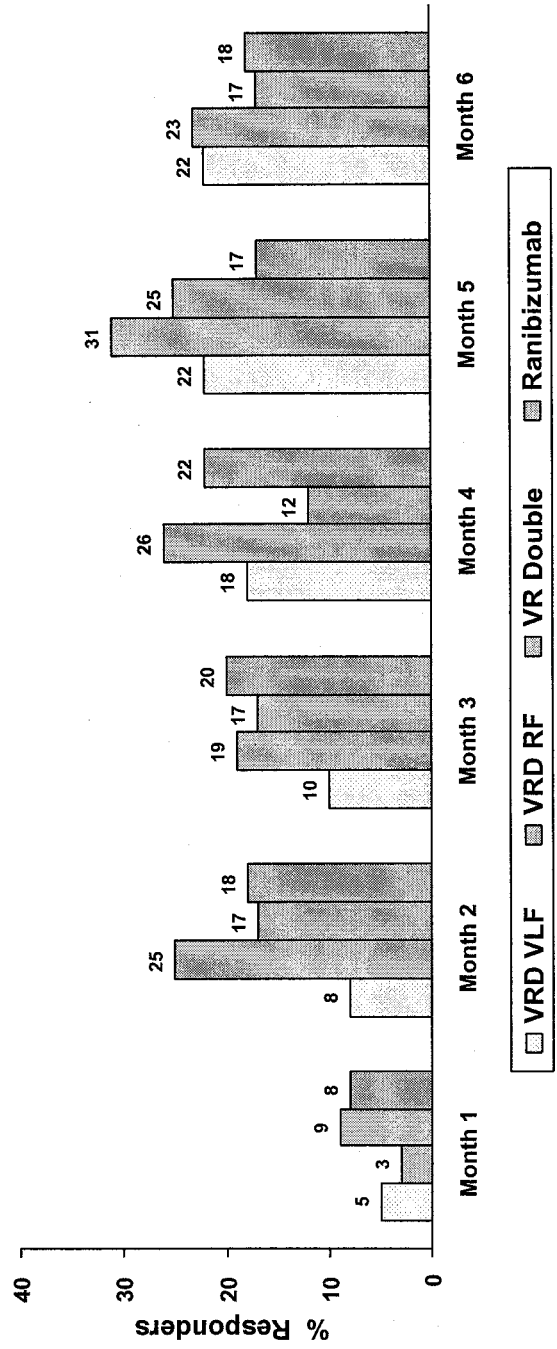
Figure 11:
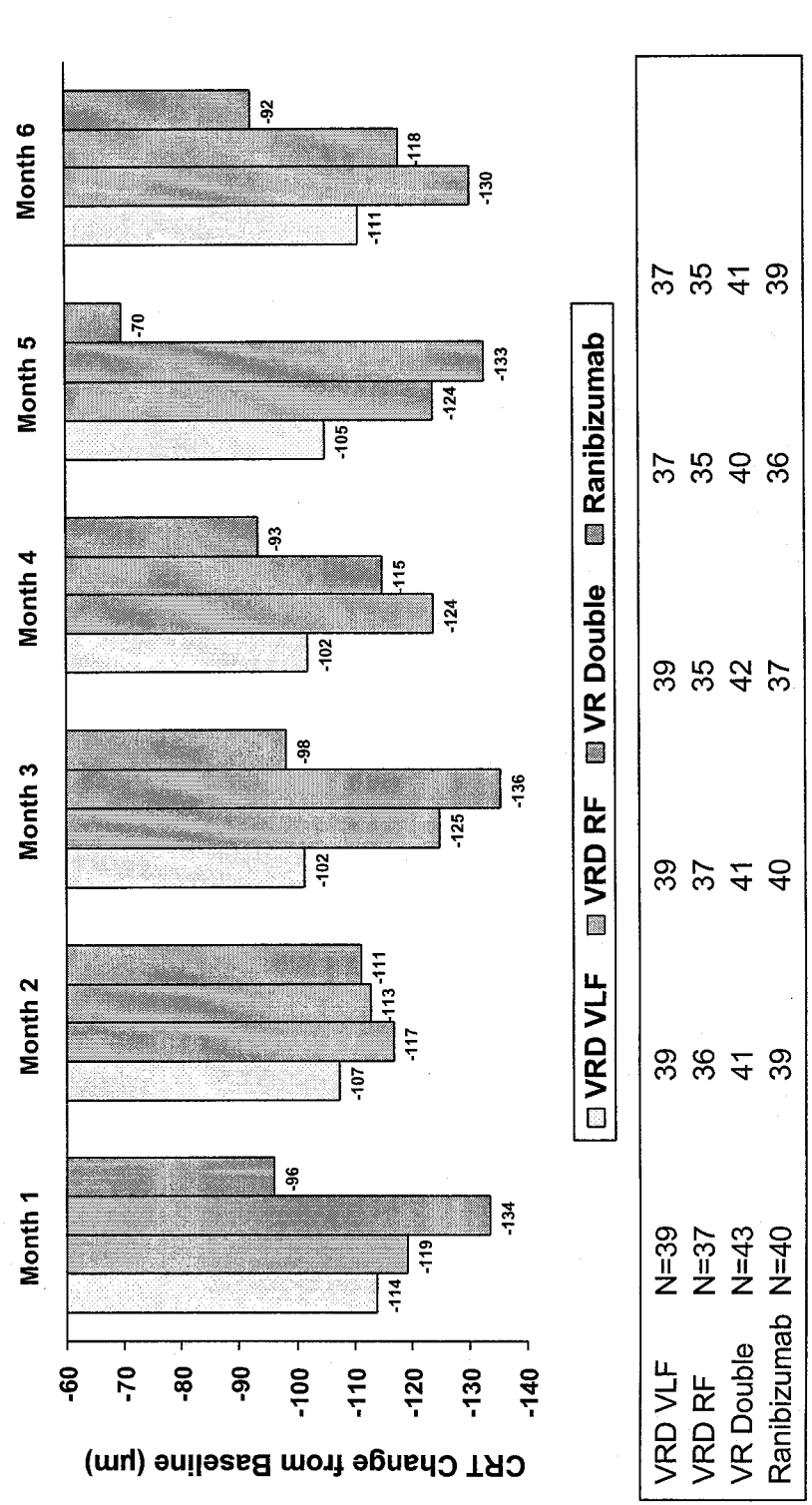
FIG. 11 shows mean change from baseline of central retinal thickness after six months of the study as described in Examples 1-3 herein.
Figure 12:
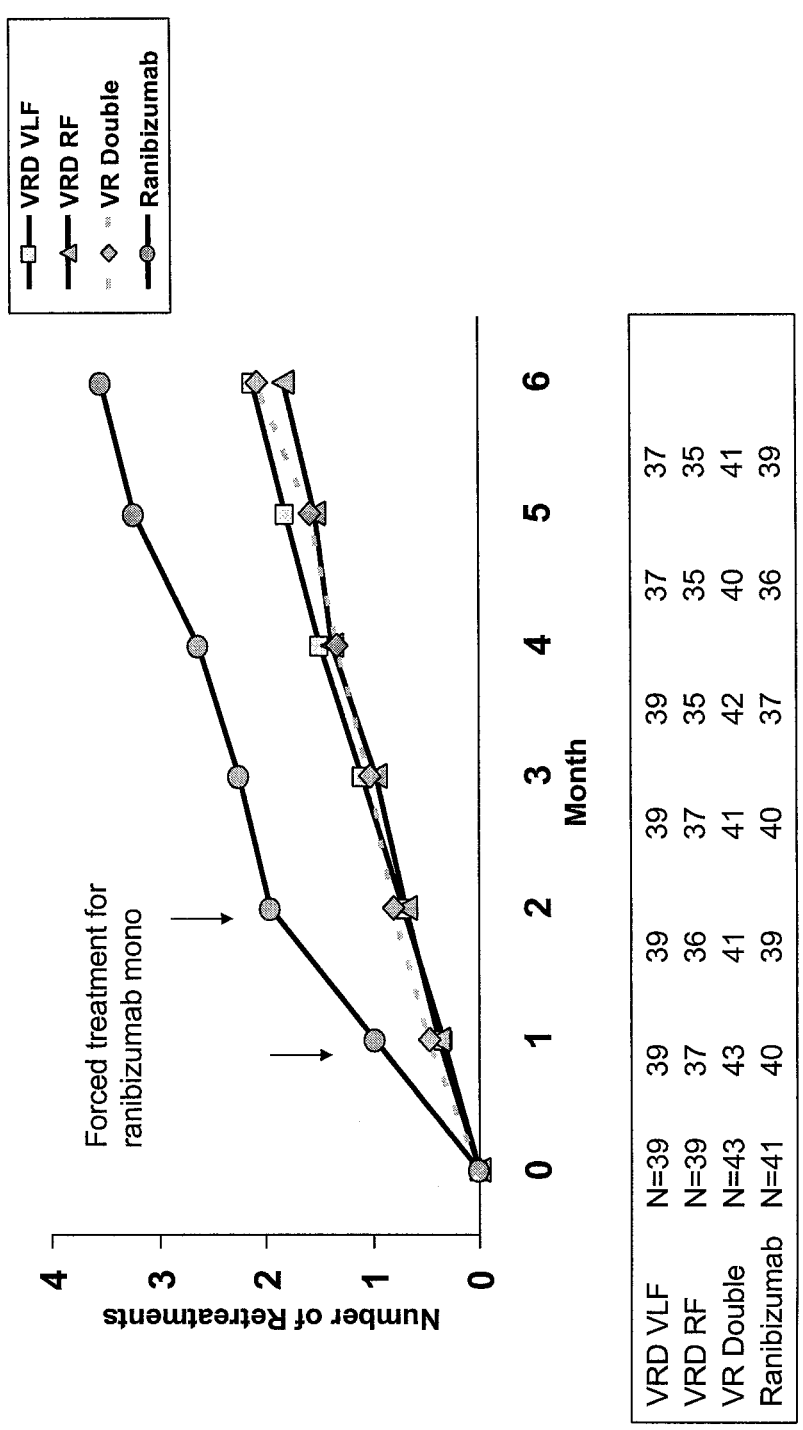
FIG. 12 shows the cumulative number of retreatments based on either OCT or FA after six months of the study as described in Examples 1-3 herein.
Figure 13:
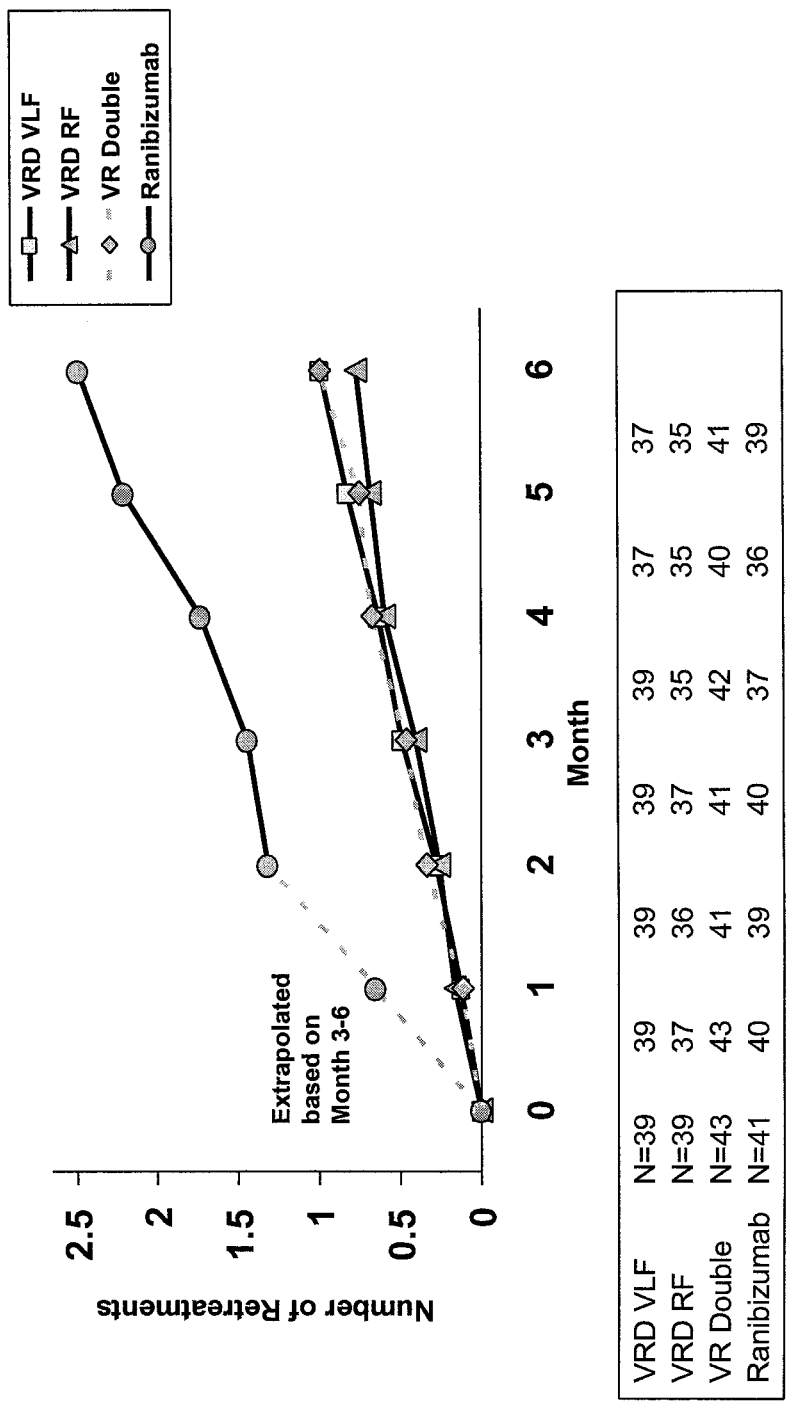
FIG. 13 shows the cumulative number of retreatments based on meeting OCT criteria after six months of the study as described in Examples 1-3 herein.
Figure 14:
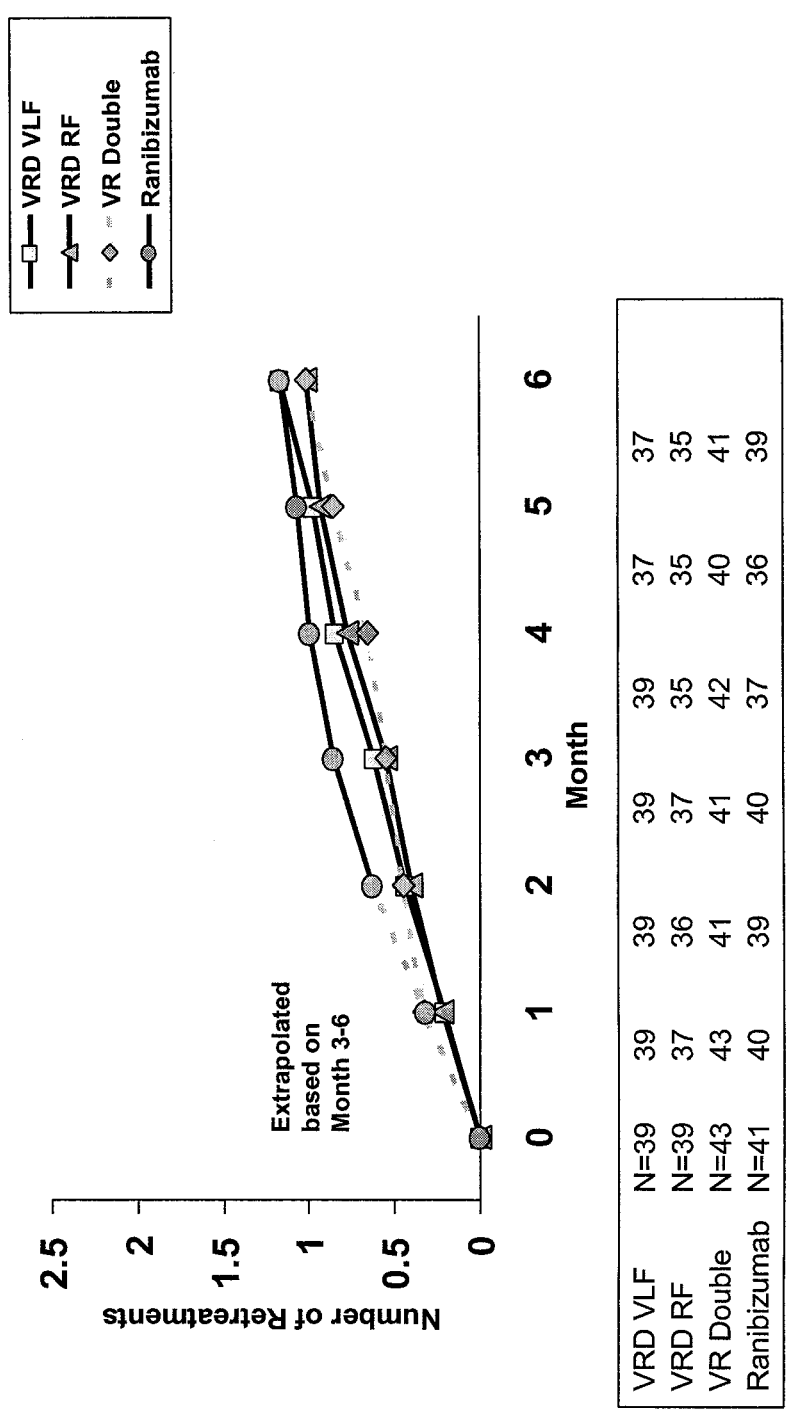
FIG. 14 shows the cumulative number of retreatments based on meeting FA criteria after six months of the study as described in Examples 1-3 herein.
Figure 15:
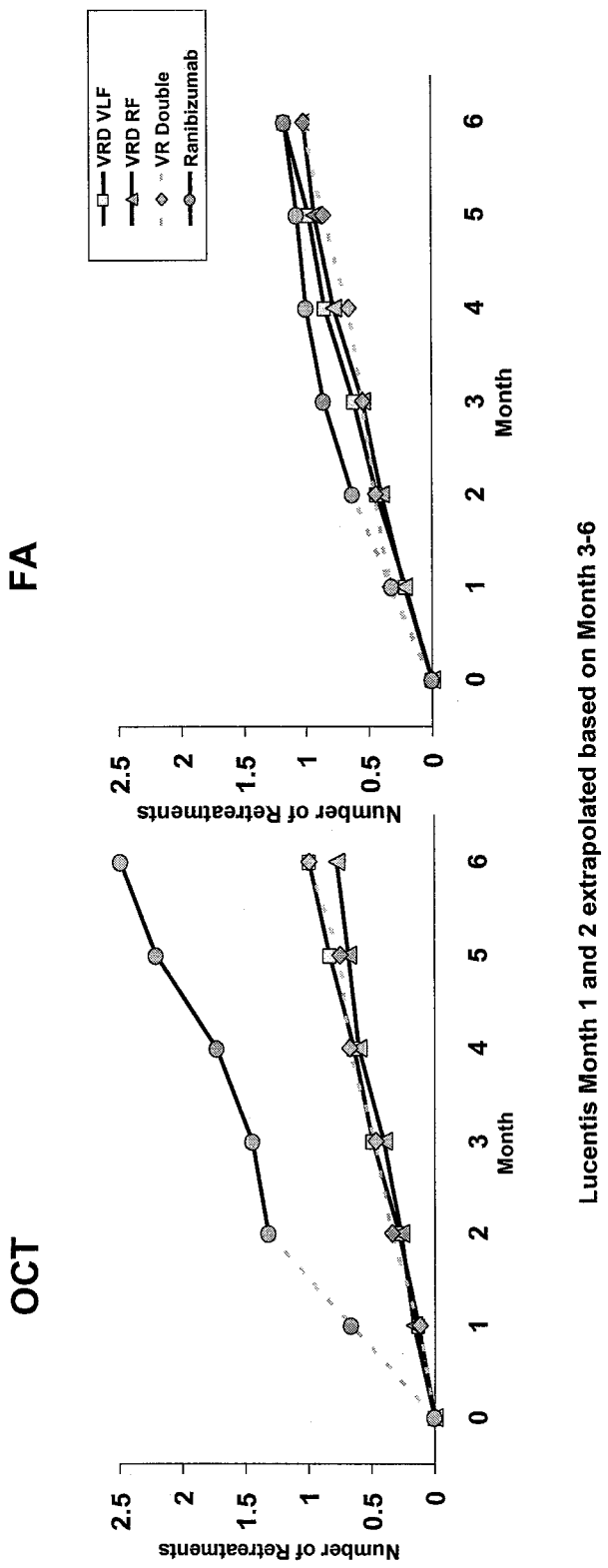
FIG. 15 shows the cumulative number of retreatments based on meeting OCT criteria vs. FA criteria after six months of the study as described in Examples 1-3 herein.

FIG. 5 presents the retreatment criteria adopted in the study.

First Year of the Study (Baseline to Month 12)

On Day 0, all subjects receive randomized treatment. Subjects randomly assigned to Lucentis monotherapy are retreated at Months 1 and 2 (with treatments ≥28 days apart). Thereafter to Month 12, Lucentis monotherapy are given as needed (pro re nata, PRN) based on retreatment criteria (FIG. 5) assessed monthly (±1 week, allowing ≥28 days between treatments). Subjects randomly assigned to combination therapy are assessed monthly to Month 12; retreatment with the assigned combination therapy is given if ≥55 days have passed since previous combination therapy and treatment is required based on retreatment criteria. If treatment is required and <55 days have passed since previous combination therapy, then subjects assigned to combination therapy receive a Lucentis injection. Lucentis injections are ≥28 days apart. No FA is needed for subjects assigned to combination therapy who meet OCT criteria for retreatment but receive a Lucentis injection because their last combination therapy was <55 days prior. FA is only used after OCT retreatment criteria are met when combination therapy is to be applied because the FA is needed to determine the lesion size and location for PDT (see FIG. 2).

All subjects have OCT at every visit; best-corrected VA testing at baseline and at Months 1-6, 9, and 12; and FA at baseline and at Months 3 and 12.

Mean number of retreatments (Day 0 treatment excluded) and mean change from baseline in best-corrected VA score are evaluated.

Second Year (Month 12 to Month 24)

Subjects attend follow-up visits at least every 3 months, primarily for safety evaluation, and are treated PRN with the therapy assigned at baseline. (As for the first year, retreatment with the assigned combination therapy is given if ≥55 days have passed since previous combination therapy and treatment is required based on retreatment criteria. If treatment is required and <55 days have passed since previous combination therapy, then subjects assigned to combination therapy receive a Lucentis injection. Lucentis injections must be ≥28 days apart). All subjects have OCT at every visit, and best-corrected VA testing at 18 and 24 months. No study treatment are given at the 24-month visit.

The combination therapy groups has assessments monthly to Month 12. Combination therapy retreatments may be given at intervals ≥55 days, based on retreatment criteria. If treatment is required at an interval <55 days, then the subject receives a Lucentis injection. It is not expected that retreatment with combination therapy will be necessary at such short intervals, but assessment is necessary to ascertain that retreatment is not required.

Randomization includes stratification by Day 0 VA (i.e. 25-50 letters and 51-73 letters) in the study eye because baseline VA is related to the rate of vision decline in subjects with AMD.

Interim Results after Six Months

Baseline characteristics of patients prior to the start of treatment are set out in FIG. 6.

After six months, mean Visual Acuity (VA) in each group was observed to increase from baseline and that increase was observed at the six month interim period to be similar between the four treatment groups (FIGS. 6 through 10).

At the first six month interim period, the Mean Cumulative Treatments received in the study were lower in the combination groups than for the Lucentis monotherapy group in the study. This data reflects the mandatory retreatments at month 1 and 2 in the Lucentis monotherapy group. At baseline, the mean best corrected visual acuity letter scores ranged from 53-58 across all treatment groups. At six months, each group had similar mean visual acuity letter score improvements from baseline (Group 1: 4.0 letters; Group 2: 7.3 letters; Group 3: 2.5 letters; Group 4: 4.4 letters) and similar reductions in retinal thickness based on OCT were observed (FIGS. 11-15). Cumulative retreatment rates were lower in all combination groups compared with the Lucentis monotherapy. This was influenced by the mandatory retreatments at months 1 and 2 in the Lucentis monotherapy group.

Combination therapy regimens in this study appeared safe based on the six month interim analysis (FIGS. 16-17).

Primary Analysis Results after Twelve Months

The overall twelve month preliminary analysis results demonstrated that fewer retreatments were required with the following combination therapies than with Lucentis monotherapy, and the differences were statistically significant.

Figure 19:
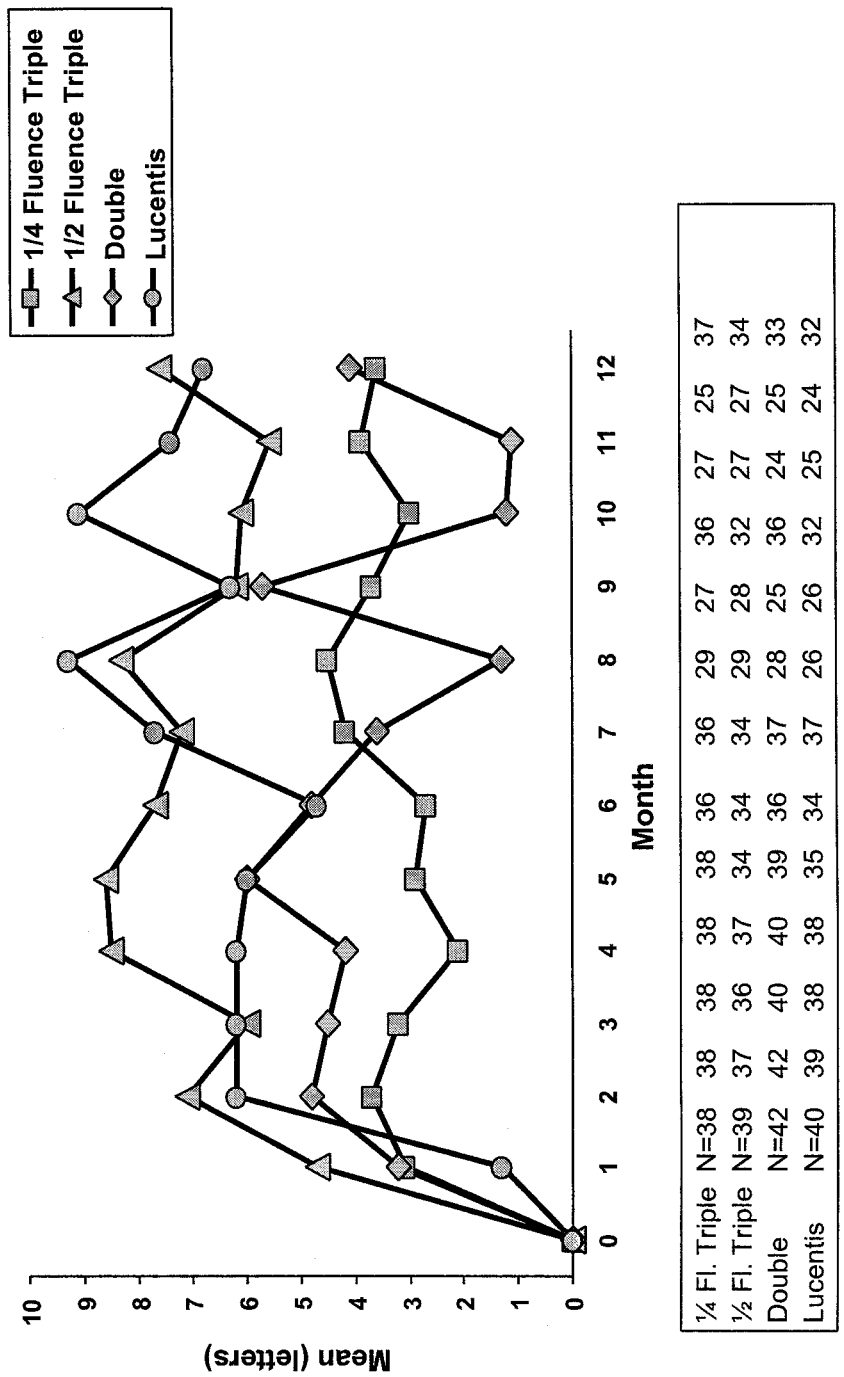

Mean visual acuity (VA) improved similarly across all treatment groups (FIGS. 19-21). Reductions in retinal thickness based on OCT were measured throughout the twelve month period (FIG. 22). There were no unexpected safety findings, and adverse event incidence at 12 months was similar across treatment groups (FIGS. 24-25).

Figure 23:
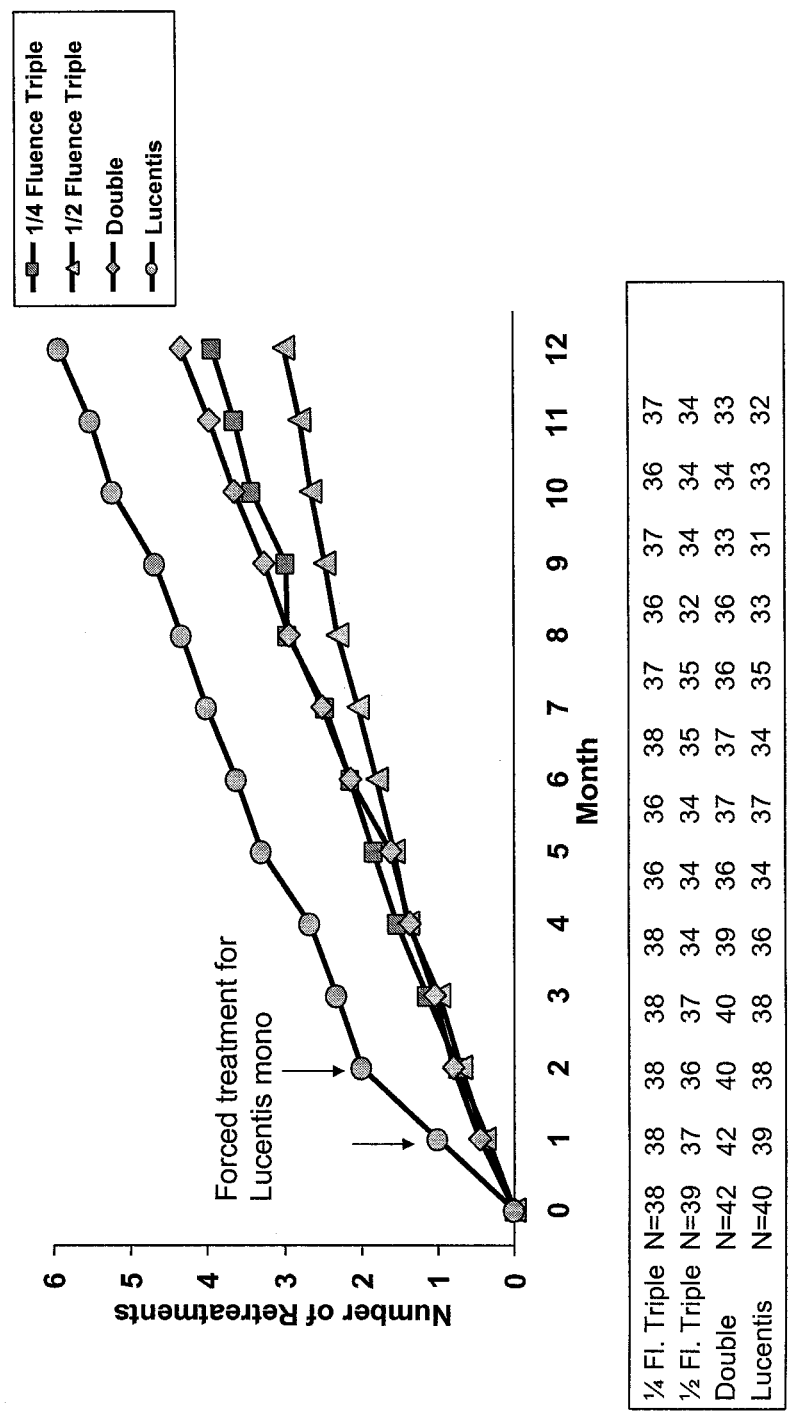
FIG. 23 shows cumulative retreatment values after twelve months of the study as described in Examples 1-3 herein.

Of the four treatment groups, the triple therapy half-fluence group demonstrated the best results, with the lowest retreatment rate and mean VA improvement most similar to Lucentis monotherapy through 12 months (FIG. 23). Patients in the triple therapy half-fluence group had a mean of 3.0 retreatments compared with 5.4 for patients who received Lucentis monotherapy (P<0.001). At the month 12 examination, mean VA in the triple therapy half-fluence group improved 6.8 letters from baseline compared with 6.5 letters in the Lucentis monotherapy group (P=0.94). Mean retreatment rates and VA improvement for each treatment group are presented in the table below. All results presented are based on ITT analyses; per-protocol analyses yielded similar results. Patients were evaluated for VA and safety, and to assess if retreatment was needed, at visits every month over 12 months of study follow-up. Overall, 10 patients discontinued the study by 12 months for reasons unrelated to Visudyne or Lucentis.

Primary Outcomes from RADICAL Study at 12 Months

| | Triple therapy | | | Lucentis monotherapy |
|---|---|---|---|---|
| | Quarter-fluence | Half-fluence | Double therapy | |
| ITT | N = 39 | N = 39 | N = 43 | N = 41 |
| Mean retreatment rate | 4.0 (P = .04) | 3.0 (P < .001) | 4.0 (P = .04) | 5.4 |
| Mean VA improvement from baseline (letters) | 3.6 (P = .38) | 6.8 (P = .94) | 5.0 (P = .63) | 6.5 |
| Per-protocol | N = 37 | N = 34 | N = 33 | N = 32 |
| Mean retreatment rate | 3.9 (P = .01) | 3.0 (P < .001) | 4.3 (P = .047) | 5.9 |
| Mean VA improvement from baseline (letters) | 3.6 (P = .38) | 7.6 (P = .84) | 4.1 (P = .46) | 6.8 |

P values are from comparison with Lucentis monotherapy

The percentage of patients whose vision improved by 3 lines or more was observed to be 31% for the half-fluence triple therapy group versus 24% for the Lucentis monotherapy group. Ocular adverse events considered associated with treatment were reported for approximately one-third of patients in the combination therapy groups, compared with approximately one-fourth of patients in the Lucentis monotherapy group. The higher incidence of these events with combination therapy was thought to be primarily due to vision disturbance events (abnormal vision and decreased vision), which are transient and known to be associated with Visudyne therapy.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method for treating unwanted choroidal neovasculature (CNV) in a human subject using photodynamic therapy (PDT), said method comprising:
   (a) administering BPD-MA to said subject afflicted with said neovasculature in an amount effective to permit an effective amount to localize in said ocular target tissue, and irradiating said target tissue with electromagnetic radiation containing a wavelength absorbable by said BPD-MA,
   (b) administering to said subject an effective amount of ranibizumab,
   wherein said administering of said ranibizumab takes place in a shortened time period subsequent to step (a), and wherein closure of CNV in said subject is effected,
   wherein said method is further selected from the group consisting of:
      i) administering BPD-MA and irradiating at 300 mW/cm$^2$ for about 83 seconds to deliver 25 J/cm$^2$, followed within about two hours by administration of intravitreal ranibizumab;
      ii) administering BPD-MA and irradiating at about 300 mW/cm$^2$ for about 83 seconds to deliver 25 J/cm$^2$, followed within about two hours by intravitreal ranibizumab, followed by administration of intravitreal dexamethasone; and
      iii) administering BPD-MA and irradiating at 180 mW/cm$^2$ for about 83 seconds to deliver 15 J/cm$^2$ followed within about two hours by intravitreal ranibizumab, followed by administration of intravitreal dexamethasone.

2. The method of claim 1, wherein said CNV is in a subject afflicted with or diagnosed with age-related macular degeneration (AMD).

3. The method of claim 2, wherein the AMD is the wet form.

4. The method of claim 3, wherein the AMD is the predominantly classic, minimally classic, or occult form.

5. The method of claim 1, wherein the PS is administered as a pharmaceutical composition selected from the group consisting of a liposome, emulsion, or aqueous solution.

6. The method of claim 1, wherein the dexamethasone is delivered intravitreally.

7. The method of claim 6, wherein said dexamethasone is administered at a dose of between about 0.4 and about 0.8 mg, and within about 2 hours of step (a), and subsequent to administration of said anti-VEGF.

8. The method of claim 1, wherein the method is repeated for a period of about at least 6 months or more following first treatment.

9. The method of claim 8, wherein the method is repeated about every three months for a period for about at least 6 months or more following first treatment.

10. The method of claim 9, wherein the method is repeated no less than about every 55 days for a period of at least 6 months following first treatment.

11. The method of claim 1, wherein visual acuity in said subject is improved.

12. The method of claim 1, wherein said method is repeated no less than about every 55 days for a period of about 6 months or more.

13. The method of claim 1, wherein the method comprises administering BPD-MA and irradiating at 300 mW/cm$^2$ for about 83 seconds to deliver 25 J/cm$^2$, followed within about two hours by intravitreal ranibizumab, followed by administration of intravitreal dexamethasone, and wherein the method is repeated about 3 times over a twelve month period.

14. The method of claim 1, wherein the method comprises administering BPD-MA and irradiating at 180 mW/cm$^2$ for about 83 seconds to deliver 15 J/cm$^2$ followed within about two hours by intravitreal ranibizumab, followed by administration of intravitreal dexamethasone, and wherein the method is repeated about four times over a twelve month period.

15. The method of claim 11, wherein the visual acuity letter score improvement from baseline after six months is at least about 2.5 letters or more.

16. The method of claim 15, wherein the visual acuity letter score improvement from baseline after six months is at least about 4 letters or more.

17. The method of claim 16, wherein the visual acuity letter score improvement from baseline after six months is at least about 7 letters or more.

18. The method of claim 1 where the shortened time period between administration of the PS and subsequent to administration of the anti-VEGF agent comprises about 2 hours.

19. The method of claim 15, wherein the visual acuity letter score improvement from baseline after six months is at least about 3.6 letters or more.

20. The method of claim 19, wherein the visual acuity letter score improvement from baseline after six months is at least about 5 letters or more.

21. The method of claim 20, wherein the visual acuity letter score improvement from baseline after six months is at least about 6.8 letters or more.

\* \* \* \* \*